United States Patent
Hathaway et al.

(10) Patent No.: US 8,136,713 B2
(45) Date of Patent: Mar. 20, 2012

(54) SURGICAL STAPLING INSTRUMENT HAVING TRANSDUCER EFFECTING VIBRATIONS

(75) Inventors: Peter Hathaway, Lebanon, CT (US); Eric Taylor, East Hampton, CT (US); Kenneth Blier, Meriden, CT (US)

(73) Assignee: Tyco Healthcare Group LP, North Haven, CT (US)

( * ) Notice: Subject to any disclaimer, the term of this patent is extended or adjusted under 35 U.S.C. 154(b) by 269 days.

(21) Appl. No.: 12/409,900

(22) Filed: Mar. 24, 2009

(65) Prior Publication Data
US 2009/0242611 A1   Oct. 1, 2009

Related U.S. Application Data

(60) Provisional application No. 61/039,131, filed on Mar. 25, 2008.

(51) Int. Cl.
*A61B 17/068* (2006.01)
(52) U.S. Cl. .............. 227/180.1; 227/176.1; 227/19; 227/175.1
(58) Field of Classification Search .......... 227/19, 227/176.1, 180.1, 175.1
See application file for complete search history.

(56) References Cited

U.S. PATENT DOCUMENTS

| | | | |
|---|---|---|---|
| 5,306,282 A | 4/1994 | Muller | |
| 5,322,055 A | 6/1994 | Davison et al. | |
| 5,658,300 A | 8/1997 | Bito et al. | |
| 5,669,922 A | 9/1997 | Hood | |
| 5,782,397 A * | 7/1998 | Koukline | 227/176.1 |
| 5,915,616 A | 6/1999 | Viola et al. | |
| 5,964,394 A | 10/1999 | Robertson | |
| 6,004,335 A | 12/1999 | Vaitekunas et al. | |
| 6,099,537 A * | 8/2000 | Sugai et al. | 606/143 |
| 6,202,914 B1 | 3/2001 | Geiste et al. | |
| 6,398,797 B2 * | 6/2002 | Bombard et al. | 606/153 |
| 6,488,196 B1 | 12/2002 | Fenton, Jr. | |
| 6,722,552 B2 * | 4/2004 | Fenton, Jr. | 227/175.1 |
| 7,168,604 B2 | 1/2007 | Milliman et al. | |
| 7,234,624 B2 | 6/2007 | Gresham et al. | |
| 7,237,708 B1 | 7/2007 | Guy et al. | |
| 7,275,674 B2 | 10/2007 | Racenet et al. | |
| 7,278,562 B2 | 10/2007 | Mastri et al. | |
| 7,293,685 B2 | 11/2007 | Ehrenfels et al. | |
| 7,296,724 B2 | 11/2007 | Green et al. | |
| 7,303,107 B2 | 12/2007 | Milliman et al. | |
| 7,823,760 B2 * | 11/2010 | Zemlok et al. | 227/175.1 |
| 2002/0190093 A1 * | 12/2002 | Fenton, Jr. | 227/176.1 |
| 2003/0009195 A1 | 1/2003 | Field et al. | |
| 2003/0229344 A1 | 12/2003 | Dycus et al. | |
| 2004/0054364 A1 * | 3/2004 | Aranyi et al. | 606/27 |
| 2005/0131390 A1 * | 6/2005 | Heinrich et al. | 606/1 |
| 2007/0149881 A1 | 6/2007 | Rabin | |
| 2009/0024161 A1 * | 1/2009 | Bonutti et al. | 606/213 |

* cited by examiner

*Primary Examiner* — Brian D Nash

(57) ABSTRACT

An end effector for a surgical instrument includes a cartridge assembly housing a plurality of fasteners, an anvil assembly operatively connected to the cartridge assembly, and a transducer operably connected to at least one of the cartridge assembly and the anvil assembly. The anvil assembly and the cartridge assembly are movable between open and closed positions. The transducer is adapted to effect vibrations along at least one of the anvil assembly and the cartridge assembly. The vibrations reduce the friction on the end effector, thereby reducing the force necessary to fire the end effector.

20 Claims, 21 Drawing Sheets

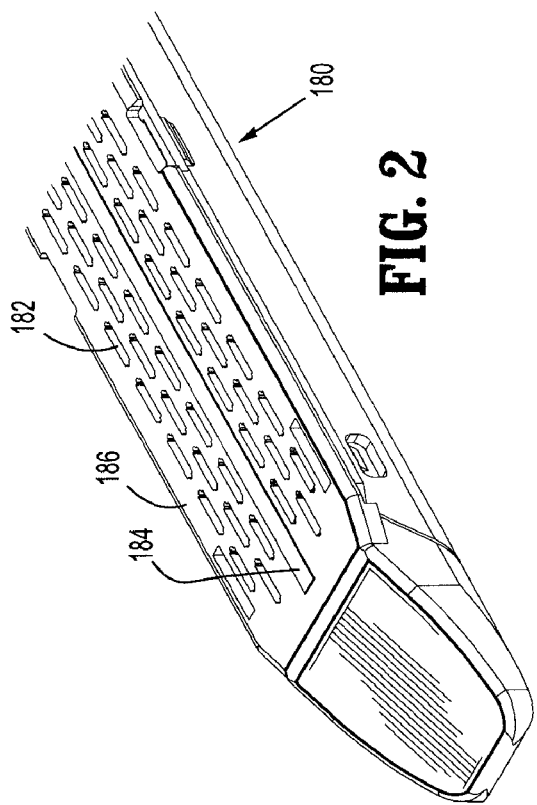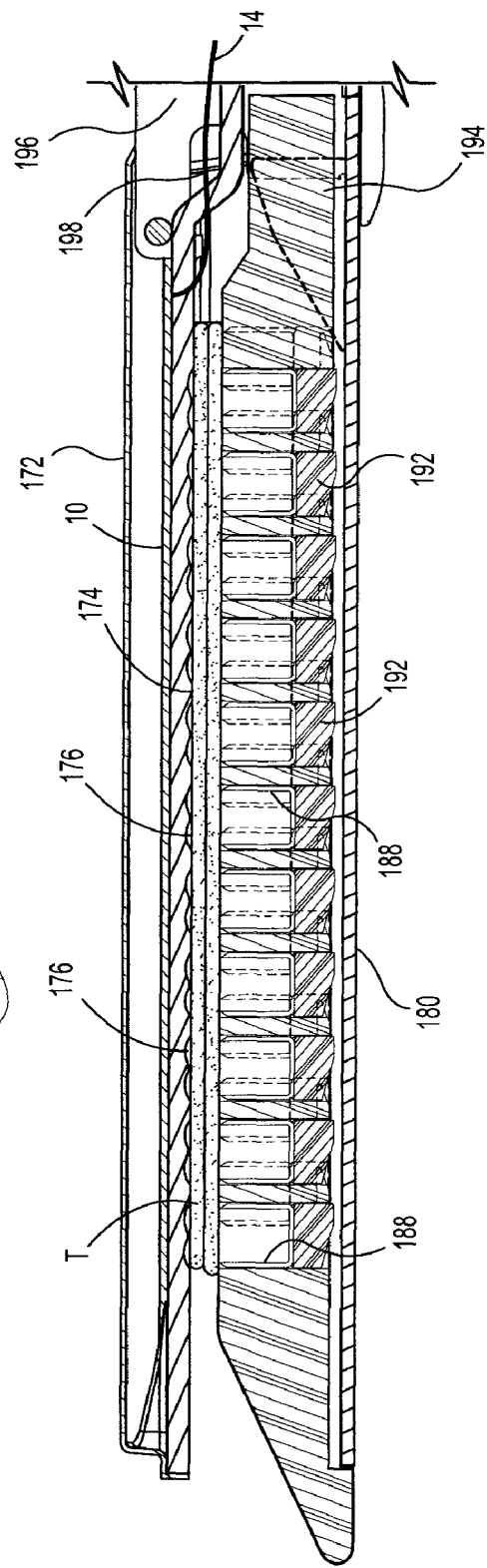

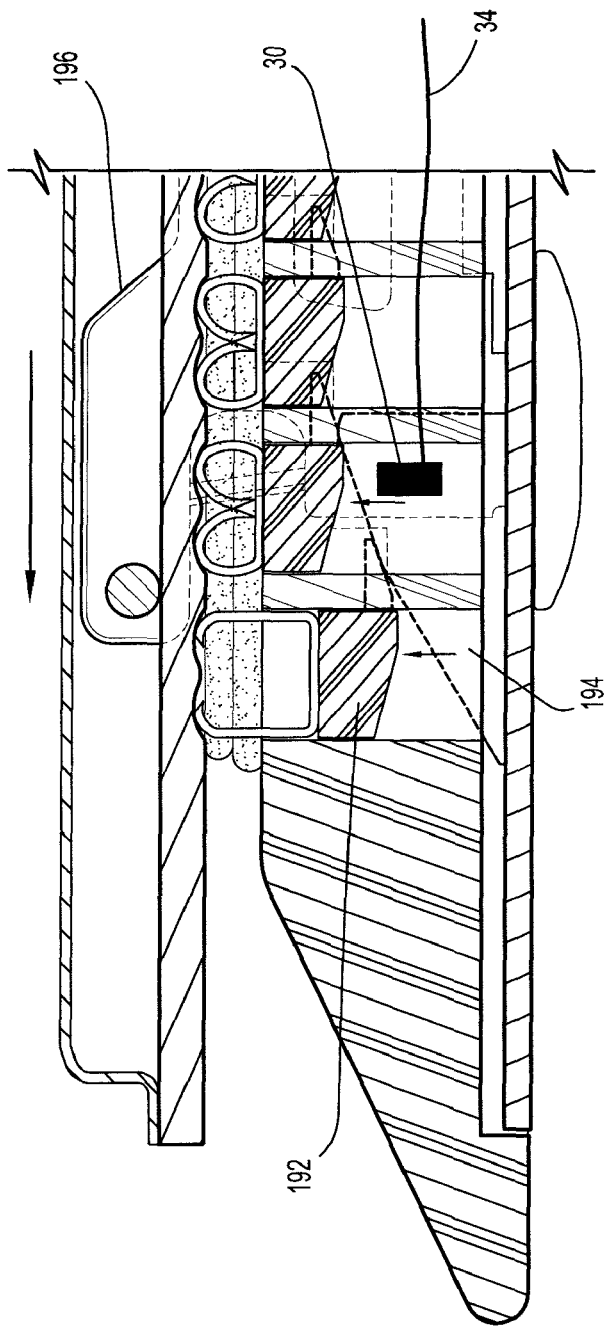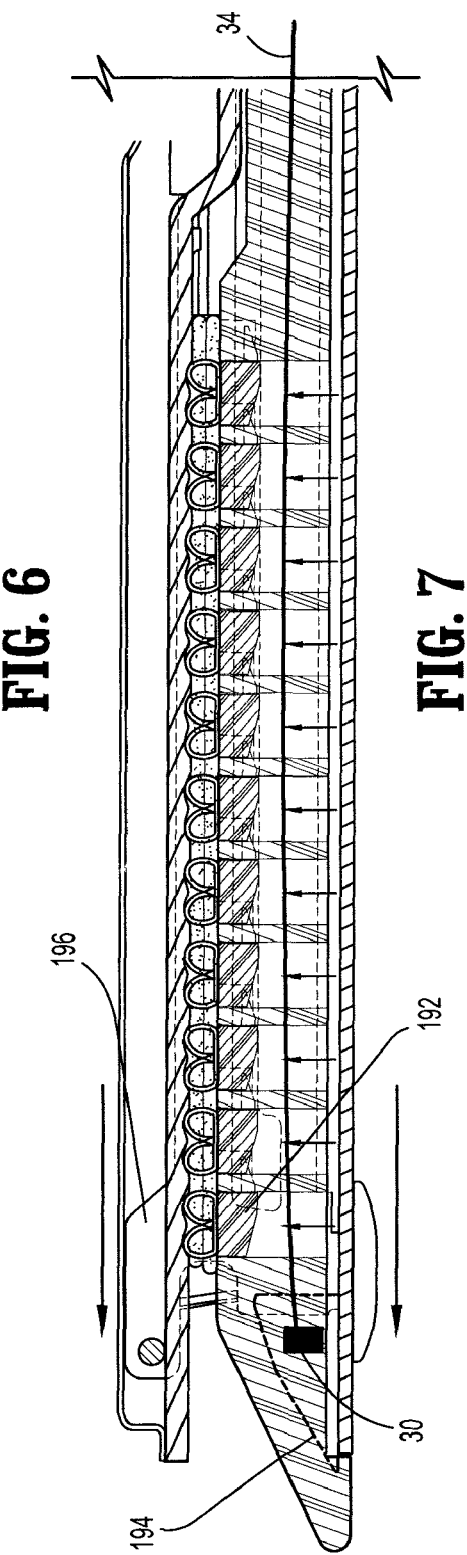
FIG. 6
FIG. 7

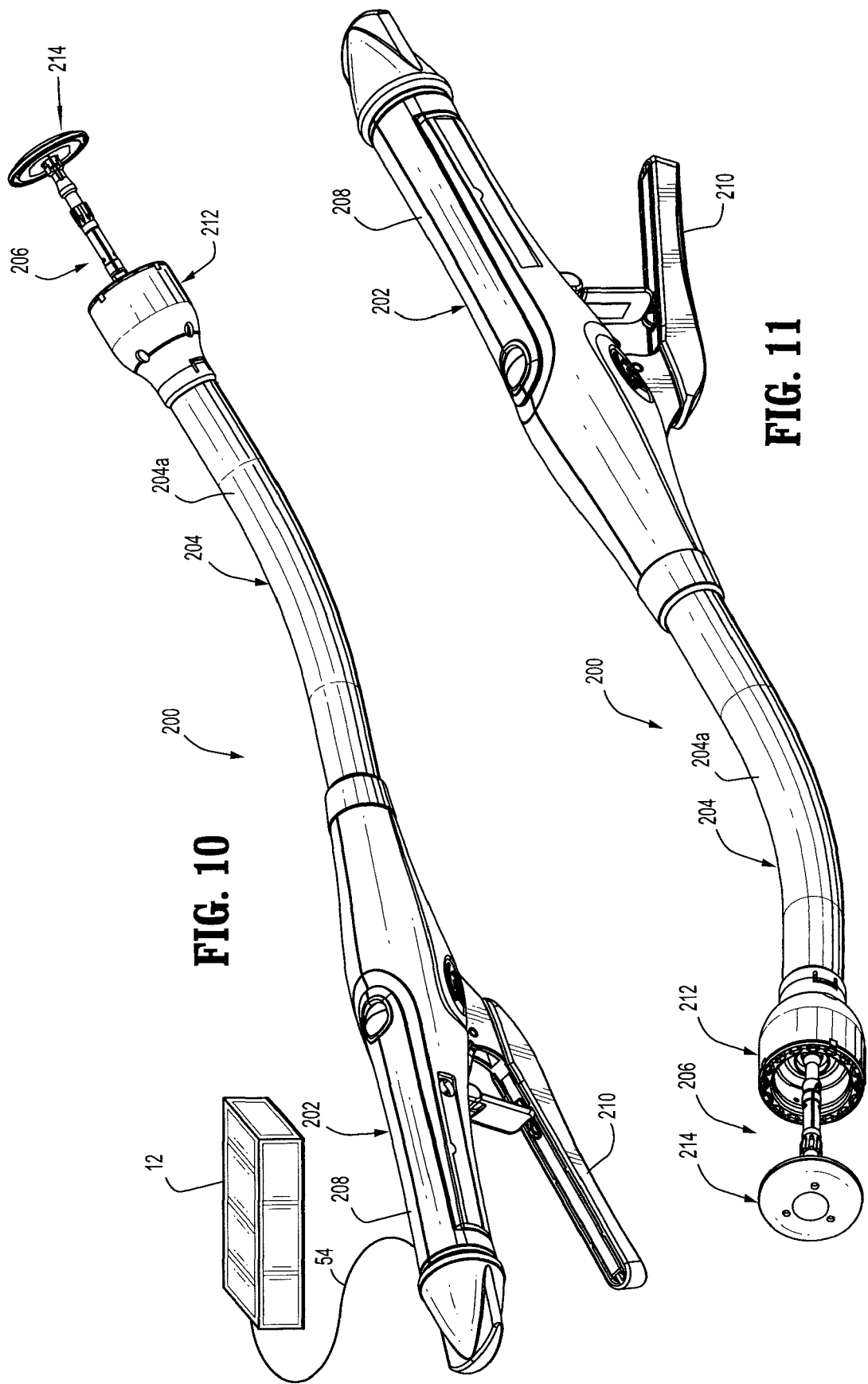

US 8,136,713 B2

SURGICAL STAPLING INSTRUMENT HAVING TRANSDUCER EFFECTING VIBRATIONS

CROSS-REFERENCE TO RELATED APPLICATION

The present application claims priority to, and the benefit of, U.S. Provisional Patent Application Ser. No. 61/039,131, filed on Mar. 25, 2008, the entire contents of which are hereby incorporated by reference.

BACKGROUND

1. Technical Field

The present disclosure relates to apparatus and methods for applying fasteners. More particularly, the present disclosure relates to surgical instruments with vibrating components.

2. Description of Related Art

The current state of the art includes numerous surgical stapling instruments adapted for various medical procedures. Some surgical stapling instruments are specifically adapted for end-to-end anastomosis, gastrointestinal anastomosis, and transverse anastomosis. U.S. Pat. Nos. 5,915,616; 6,202,914; and 5,964,394 describe examples of these surgical stapling instruments Typically, surgical stapling instruments include an anvil that is approximated relative to a staple cartridge. The staple cartridge usually has one or more laterally spaced rows of staples. These rows of staples may be arranged in a linear or non-linear configuration. In use, a surgical stapling instrument initially clamps tissue portions and ejects fasteners such as staples. The fasteners then pass through the clamped tissue portions and form completed staples as they contact the fastener deforming depressions on the anvil. Some surgical stapling instruments include a knife positioned on the cartridge to cut tissue during anastomosis.

Although many surgical instruments have been developed over the years, improvements are still possible. For example, a need exists for surgical stapling instrument that can further enhance the stapling process.

SUMMARY

The present disclosure relates to an end effector for a surgical instrument. This end effector includes a cartridge assembly housing a plurality of fasteners, an anvil assembly operatively connected to the cartridge assembly, and a transducer operably connected to at least one of the cartridge assembly and the anvil assembly. The anvil assembly and the cartridge assembly are movable between open and closed positions. The transducer is adapted to effect vibrations along at least one of the anvil assembly and the cartridge assembly. The vibrations reduce the friction on the end effector, thereby reducing the force necessary to fire the end effector.

The present disclosure further relates to a surgical instrument. This surgical instrument includes a handle assembly, an axial drive assembly operably coupled to the handle assembly, an end effector operatively connected to the axial drive assembly, and at least one transducer disposed in the end effector. The axial drive assembly is configured to move longitudinal upon actuation of the handle assembly. The end effector has an anvil assembly and a cartridge assembly. The cartridge assembly is configured to house a plurality of fasteners. The anvil assembly and the cartridge assembly are adapted to move relative to each other between an open position and a closed position. The at least one transducer is configured to effect vibrations along at least a portion of the end effector. In operation, the vibrations reduce the friction on the end effector during firing, thereby reducing the force necessary to fire the end effector.

BRIEF DESCRIPTION OF THE DRAWINGS

Embodiments of the presently disclosed surgical stapling instruments are described herein with reference to the accompanying drawings, wherein:

FIG. 2 is a perspective view of a distal portion of a tool assembly of the surgical stapling instrument shown in FIG. 1;

FIG. 3 is a side cross-sectional view of the tool assembly of the surgical stapling instrument shown in FIG. 1 with a transducer operatively connected to the anvil assembly;

FIG. 6 is a side cross-sectional view of a distal portion of the tool assembly of the surgical stapling instrument shown in FIG. 1 including a transducer positioned on the actuation sled;

FIG. 7 is a side cross-sectional view of the tool assembly of the surgical stapling instrument shown in FIG. 1 including a transducer positioned on the actuation sled;

FIG. 10 is a perspective view of a surgical stapling instrument according to an embodiment of the present disclosure with an external power source attached thereto;

FIG. 11 is a perspective view of the surgical stapling instrument shown in FIG. 10 without an external power source;

DETAILED DESCRIPTION OF THE EMBODIMENTS

Figure 1:
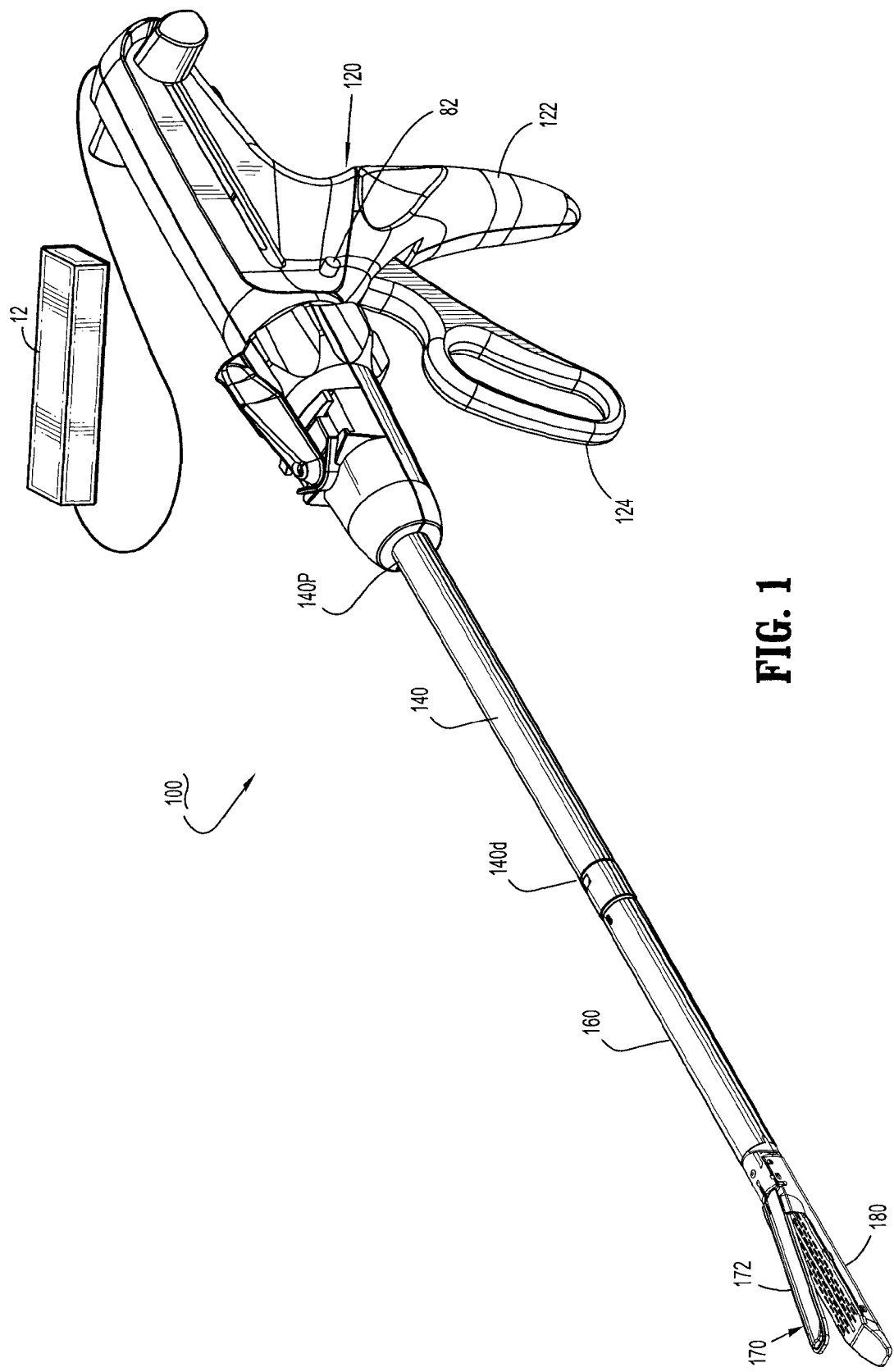
FIG. 1 is a perspective view of a surgical stapling instrument constructed in accordance with an embodiment of the present disclosure.

Embodiments of the presently disclosed surgical stapling instruments will now be described in detail with reference to the drawings, wherein like reference numerals identify similar or identical elements. In the drawings and in the description that follows, the term "proximal," as is traditional, will refer to the end of the surgical stapling instrument that is closest to the operator while the term "distal" will refer to the end of the device that is farthest from the operator.

With reference to FIG. 1, a surgical stapling instrument according to an embodiment of the present disclosure is generally designated with reference character 100. In the interest of brevity, the present disclosure focuses on apparatus and methods for effecting vibrations along at least a portion of a surgical stapling instrument. U.S. Pat. No. 7,303,107, the entire contents of which are incorporated by reference herein, describes in detail the construction and operation of the surgical stapling instrument illustrated in FIG. 1. Other kinds of surgical instruments may nonetheless incorporate vibrating components, as discussed hereinbelow.

Surgical stapling instrument 100 generally includes a handle assembly 120, an elongated body 140, and a loading unit 160. Handle assembly 120 has stationary handle member 122 and a movable handle member 124 adapted to move in relation to the stationary handle member 122. In operation, a user moves movable handle member 124 toward stationary handle member 122 to actuate loading unit 160. Alternatively, surgical stapling instrument 100 may include any other suitable mechanism for actuating loading unit 160.

Elongated body 140 interconnects handle assembly 120 and loading unit 160 and has a cylindrical shape. A proximal end 140p of elongated body 140 is operatively secured to handle assembly 120, whereas a distal end 140d of elongated body 104 is releasably fixed to loading unit 160.

Loading unit 160 contains a tool assembly 170 having an anvil assembly 172 and a cartridge assembly 180. Anvil assembly 170 is configured to move relative to cartridge assembly 180 to clamp tissue upon actuation of handle assembly 120. As shown in FIGS. 2 and 3, cartridge assembly 180 has a plurality of rows of retention slots 182, a knife channel 184 positioned between the rows of retentions slots 182, and a tissue contacting surface 186. Each retention slot 182 houses a staple 188 and a staple pusher 192. Cartridge assembly 180 also includes an actuation sled 194 operatively coupled to an axial drive assembly 196. Axial drive assembly 196 is in mechanical cooperation with handle assembly 120 and includes a knife edge 198 formed thereon. Upon actuation of handle assembly 120, axial drive assembly 196 urges actuation sled 194 through cartridge assembly 180 in a distal direction. As actuation sled 194 translates through cartridge assembly 180, it drives staple pushers 192 upwardly. The upward movement of staple pushers 192 consequently causes the ejection of staples 188 from cartridge assembly 180. In addition to the ejection of staples 180, as axial drive assembly 196 advances distally, knife edge 198 moves along knife channel 184 to sever the tissue clamped between cartridge assembly 180 and anvil assembly 172.

Figure 3A:
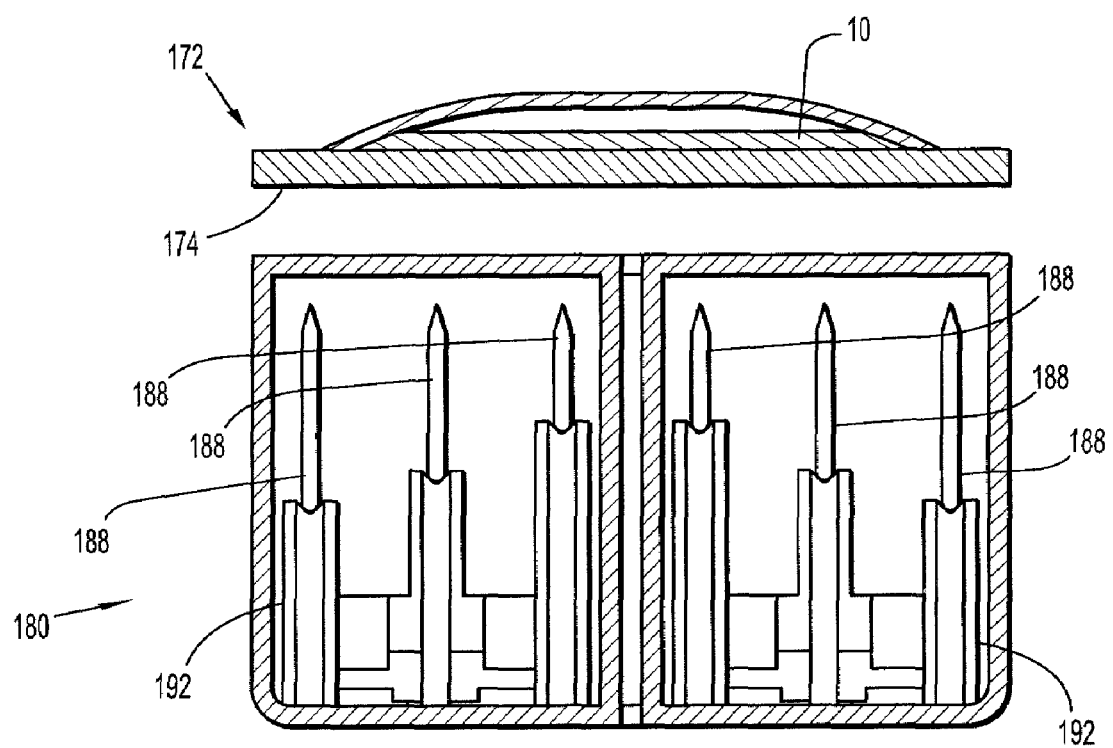
FIG. 3A is a front cross-sectional view of the tool assembly of the surgical stapling instrument shown in FIG. 1 with a transducer operatively attached to the anvil assembly.

Anvil assembly 172 is adapted to move in relation to cartridge assembly 180 between an open position (see FIG. 1) and a closed position (see FIG. 3). When anvil assembly 172 is in the open position, tool assembly 170 can receive tissue between cartridge assembly 180 and anvil assembly 172. On the other hand, when a user moves anvil assembly 172 from the open position to the closed position, tool assembly 170 clamps the tissue "T" placed between cartridge assembly 180 and anvil assembly 172. Like cartridge assembly 180, anvil assembly 172 includes a tissue contacting surface 174. (See FIGS. 3A and 9A). The tissue contacting surface 174 of anvil assembly 172, however, contains staple deforming cavities 176 for forming staples during the ejection process.

In one embodiment, anvil assembly 172 additionally includes a transducer 10 positioned therein, as seen in FIGS. 3 and 3A. Transducer 10 extends along at least a portion of the length of tissue contacting surface 174 and is operatively connected to a power source 12 (see FIG. 1). Wires 14 or any other suitable connecting device operatively couples power source 12 and transducer 10. Power source 12 supplies transducer 10 the energy necessary to effect vibrations along anvil assembly 172. During operation, transducer 10 converts electrical energy into vibrational motion along anvil assembly 172. Transducer 10 may be formed of one or more piezoelectric ceramic element such as lead zirconium titanate, potassium niobate, lithium niobate, lithium tantalate or the like. A transducer 10 made of piezoelectric ceramic elements generates high frequency, low amplitude vibrations when energized with a high frequency, alternating voltage and current. Optionally, anvil assembly 172 may further include a resonant member (not shown) connected to transducer 10. The optional resonant member is made of material capable of vibrating when transducer 10 vibrates. Alternatively, anvil assembly 172 may include a plurality of transducers placed along selected portions of the anvil assembly 172. These transducers are adapted to vibrate sequentially from the proximal end to the distal end of anvil assembly 172 as the axial drive assembly 196 moves in a distal direction. In this embodiment, axial drive assembly 196 contains electrical contacts to sequentially transmit electrical energy from power source 12 to each transducer located along anvil assembly 172.

In operation, the vibrations produced by transducer 10 vibrate anvil assembly 172. The vibrations of anvil assembly 172 propagate through the clamped tissue, cartridge assembly 180, and staples 188 during the stapling process. These vibrations reduce the frictional forces experienced between anvil assembly 172, cartridge assembly 180, and clamped tissue, thereby reducing the amount of force necessary to actuate the tool assembly 170. Additionally, the vibrations of the anvil assembly 172 impart a component of displacement into the direction of the tissue. Such displacement causes the staple to penetrate the tissue using less force.

Figure 4:
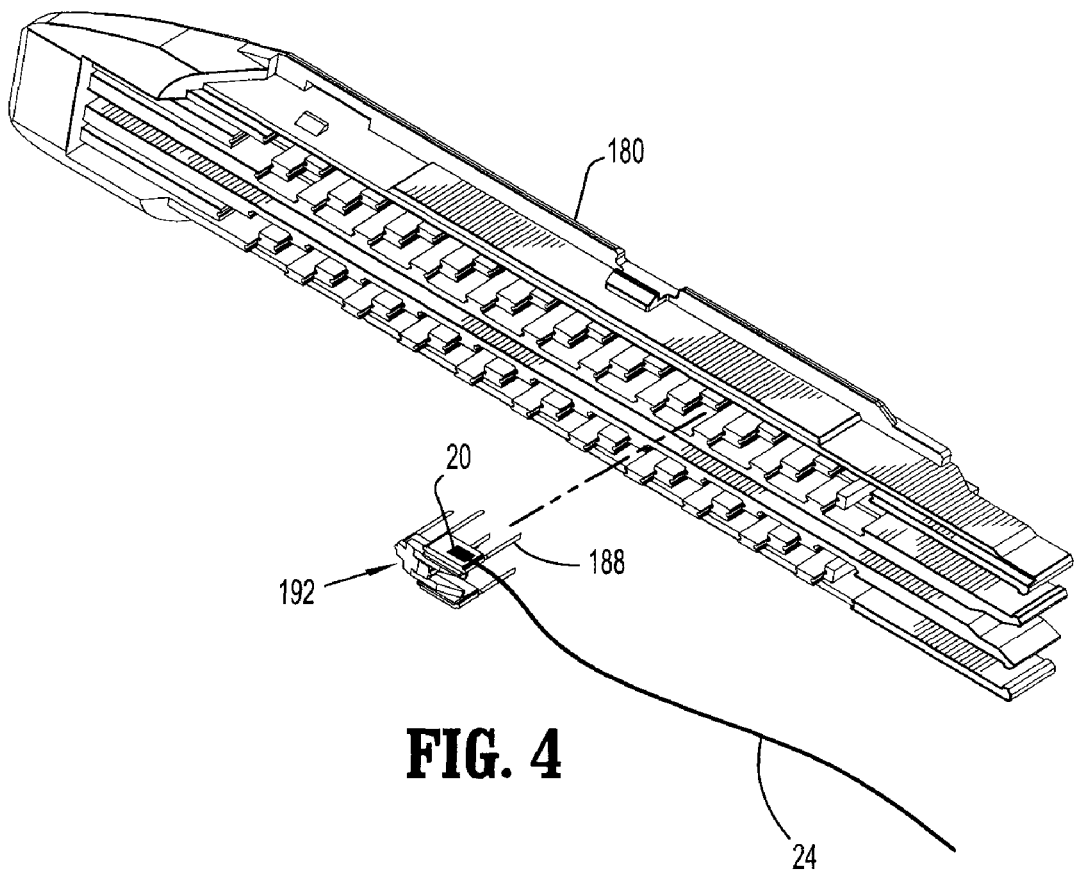
FIG. 4 is a perspective exploded view of a cartridge assembly, a staple pusher, and staples of the surgical stapling instrument shown in FIG. 1.
Figure 5:
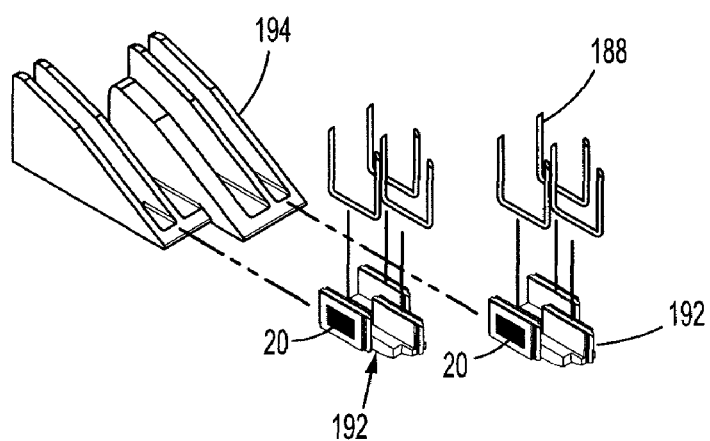
FIG. 5 is a perspective view of an actuation sled, staple pushers, and staples of the surgical stapling instrument shown in FIG. 1.

Referring to FIGS. 4 and 5, in another embodiment, at least one staple pusher 192 includes a transducer 20 attached thereto. Transducer 20 is operatively connected to power source 12 (see FIG. 1) and may be composed of piezoelectric ceramic elements. Wires 24 or any other suitable connecting device interconnects power source 12 and transducers 20. In an alternative embodiment, power source 12 is electrically connected to actuation sled 194 through an electrical contact disposed along cartridge assembly 180. Actuation sled 194 has other electrical contacts configured to establish an electrical connection between actuation sled 194 and transducers 20 as actuation sled 194 translates distally through cartridge assembly 180. Consequently, power source 12 energizes transducers 20 sequentially as actuation sled 194 advances from a proximal portion to a distal portion of cartridge assembly 180.

When power source 12 energizes transducers 20, transducers 20 effect vibrations on staple pushers 192. The vibrations of staple pushers 192 spread through the cartridge assembly 180 and staples 188 during the stapling process. The vibrational movement of staple pushers 192, cartridge assembly 180, and staples 188 decrease the frictional forces therebetween and thus reduce the force required to insert staples 188 through tissue. In addition, the vibrations of staple pushers 192 impart a component of displacement in the direction of the tissue and causes staples 188 to penetrate the tissue using less force.

With reference to FIGS. 6 and 7, another embodiment of surgical stapling instrument 100 includes at least one transducer 30 fixed to actuation sled 194. Transducer 30 is operatively coupled to power source 12. Wires 34 or any other suitable connecting device interconnects power source 12 (FIG. 1) and transducer 30. Alternatively, power source 12 is electrically coupled to transducer 30 through electrical connectors disposed in axial drive assembly 196. Transducer 30 is configured to convert electrical energy into mechanical vibrations and may be made of piezoelectric ceramic elements.

During operation, transducer 30 vibrates and effect vibrations on actuation sled 194 when energized by power source 12. The vibrations of actuation sled 194 propagate to staple pushers 192 as actuation sled 194 advances through cartridge assembly 180. In turn, the vibrations of staple pushers 192 cause the staples 188 to vibrate during its upward motion toward the clamped tissue. The vibrational movement of the actuation sled 192, staple pushers 192, and staples 188 reduces friction and therefore decreases the amount of force required to fire staples 188. Furthermore, the vibrations of actuation sled 192 impart a component of displacement in the direction of the tissue and causes staples 188 to penetrate the tissue using less force.

Figure 8:
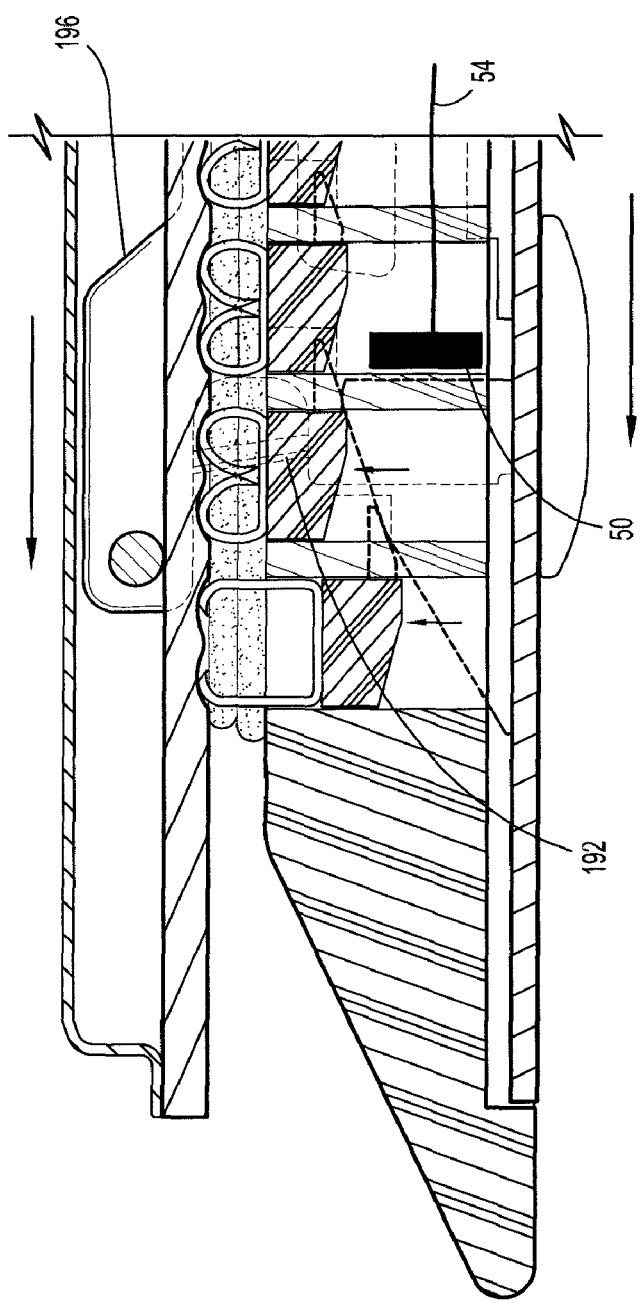
FIG. 8 is a side cross-sectional view of a distal portion of the tool assembly of the surgical stapling instrument shown in FIG. 1 with a transducer located on the axial drive assembly.
Figure 9:
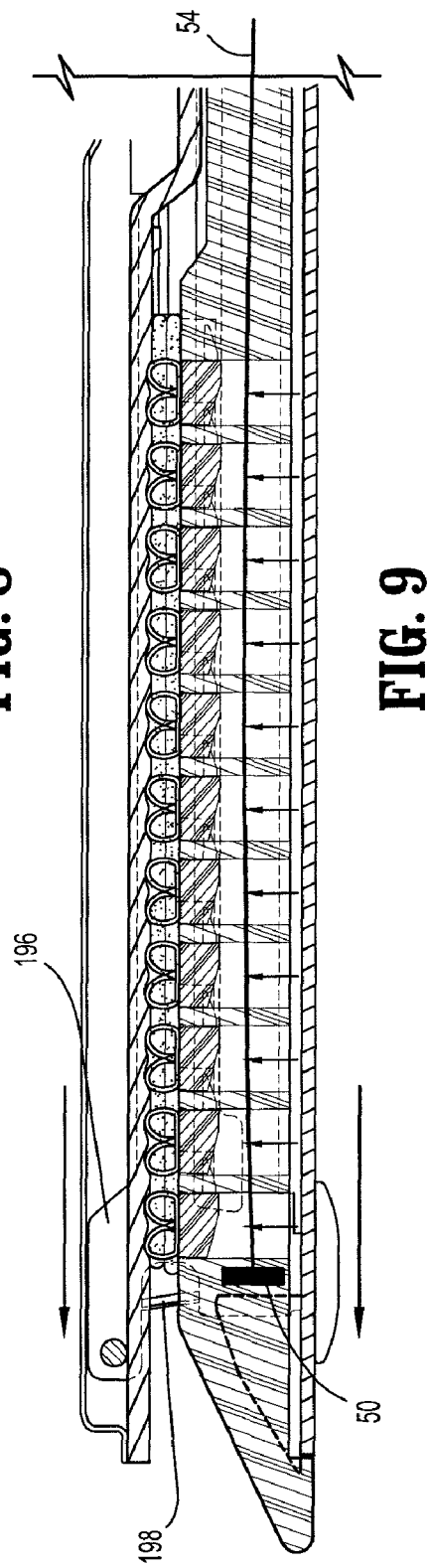
FIG. 9 is a side cross-sectional view of the tool assembly of the surgical stapling instrument shown in FIG. 1 including a transducer located on the axial drive assembly.
Figure 9A:
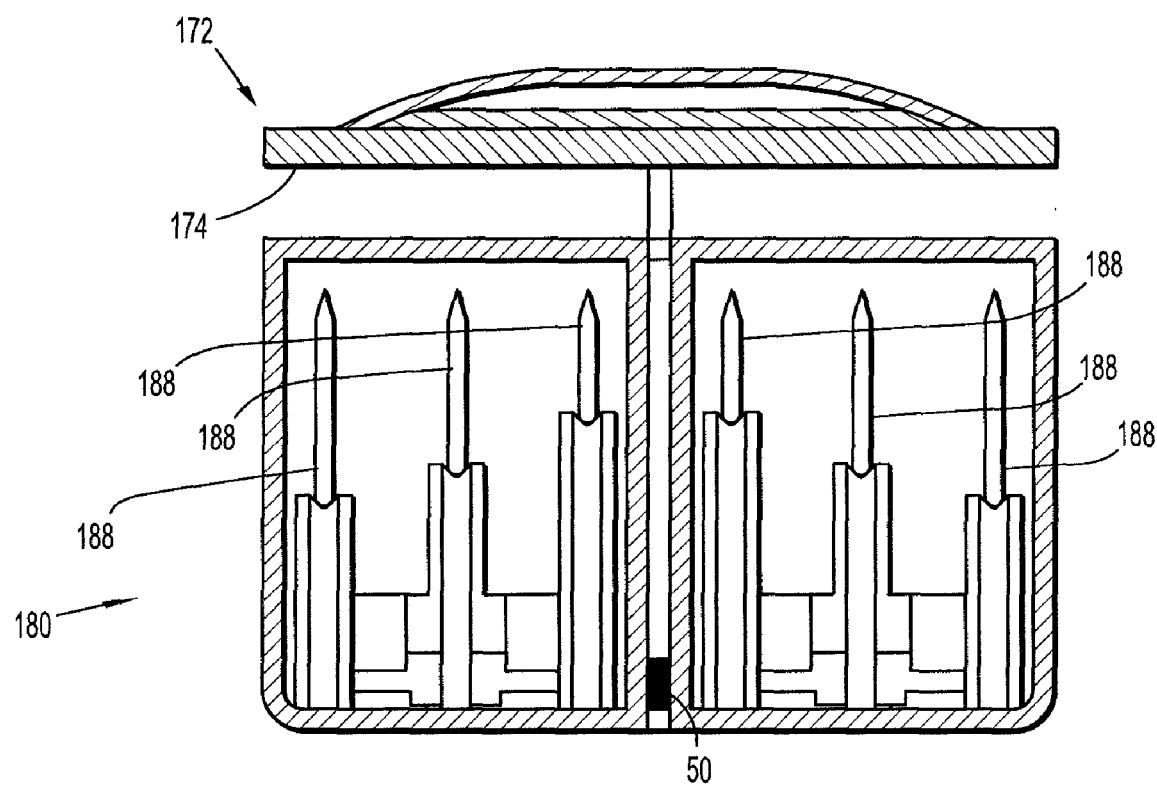
FIG. 9A is a front cross-sectional view of the tool assembly of the surgical instrument shown in FIG. 1 including a transducer located on the axial drive assembly.

With reference to FIGS. 8, 9, and 9A, still another embodiment of surgical stapling instrument 100 incorporates a transducer 50 attached to axial drive assembly 196. Axial drive assembly 196 electrically connects power source 12 (FIG. 1) to transducer 50. Alternatively, wires 54 connect power source 12 (see FIG. 1) to transducer 50. Power source 12 supplies energy to transducer 50.

During operation, transducer 50 transforms the electrical energy supplied by power source 12 into mechanical vibrations. The vibrations of transducer 50 cause the vibration of axial drive assembly 196 and knife edge 198. As a result of the vibrations of knife edge 198, the friction inside cartridge assembly 180 decreases and consequently the amount of force required to cut through tissue decreases. The vibrations of knife edge 198 also reduce bleeding. In addition, the vibrations of transducer 50 impart a component of displacement in the direction of the tissue, thereby facilitating the penetration of tissue by staples 188.

Referring to FIGS. 10 and 11, a surgical stapling instrument in accordance with an embodiment of the present disclosure is generally designated as 200. U.S. Pat. No. 7,168,604, the entire contents of which are incorporated by referenced herein, thoroughly describes the construction and operation of the surgical stapling instrument 200. In brief, surgical stapling instrument 200 includes a handle assembly 202, an elongated central body portion 204, a tool assembly 206, and wires 54 operatively coupling surgical stapling instrument 200 to a power source 12. Although the drawings show power source 12 located outside surgical stapling instrument 200, power source 12 may be positioned inside surgical stapling instrument 200. Handle assembly 202 contains a stationary handle member 208 and a movable handle member 210. Movable handle member 210 is adapted to move relative to stationary handle member 208. In operation, a user approximates movable handle member 210 toward stationary handle member 208 to actuate tool assembly 206.

Central body portion 204 has an outer tube 204a operatively connecting tool assembly 206 and handle assembly 202. Tool assembly 206 includes a cartridge assembly 212 and an anvil assembly 214. Anvil assembly 214 is releasably secured to cartridge assembly 212 and has staple deforming cavities 226 (see FIG. 15). In use, the actuation of handle assembly 202 causes anvil assembly 214 to move relative to cartridge assembly 212 and clamp tissue.

Figure 12:
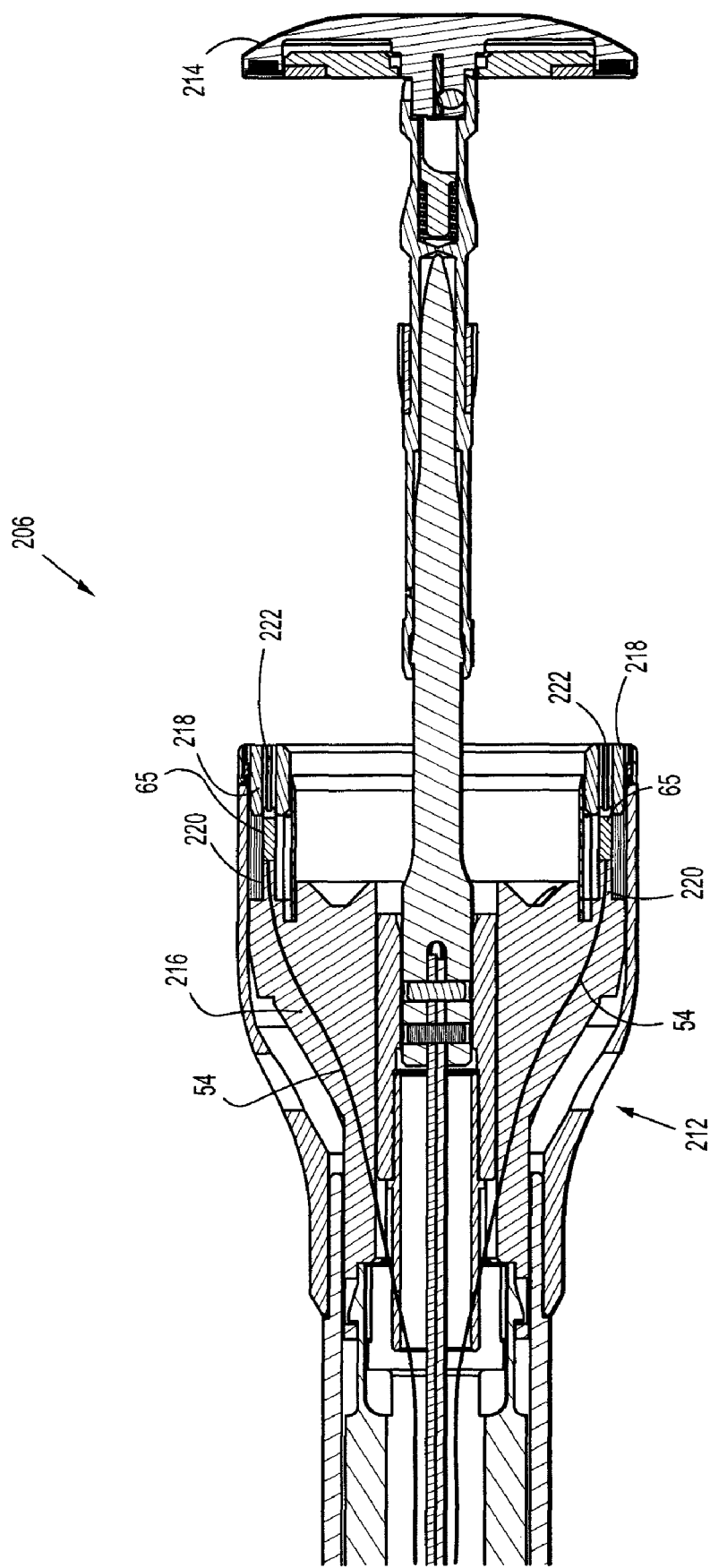
FIG. 12 is a side cross-sectional view of a distal portion of the surgical stapling instrument shown in FIG. 10 with transducers attached to the fingers of the staple guide.

With reference to FIG. 12, cartridge assembly 212 includes a staple pusher 216 and retention slots 218. Staple pusher 216 includes fingers 220 protruding distally therefrom. Each retention slot 218 houses a staple 222 and is adapted to receive a finger 220. When a user actuates handle assembly 202, staple pusher 216 moves distally along with fingers 220. Fingers 220, in turn, translate distally into retention slots 218 and eject staples 222. In the embodiment depicted in FIG. 12, transducers 65 are located on a distal portion of fingers 220. Wires 54 operatively connect transducers 65 to power source 12 (FIG. 10). Power source 12 supplies energy to transducers 65. Transducers 65 are configured to convert electrical energy into mechanical vibrations.

When energized, transducers 65 vibrate and impart vibrations on fingers 220 and staples 222. The vibrations of fingers 220 and staples 222 reduce friction and thus reduce the amount of force required to eject staples 222. Also, the vibrations of transducers 65 intermittently displace staples 222 toward the tissue and allow the staples 222 to penetrate tissue using less force.

Figure 13:
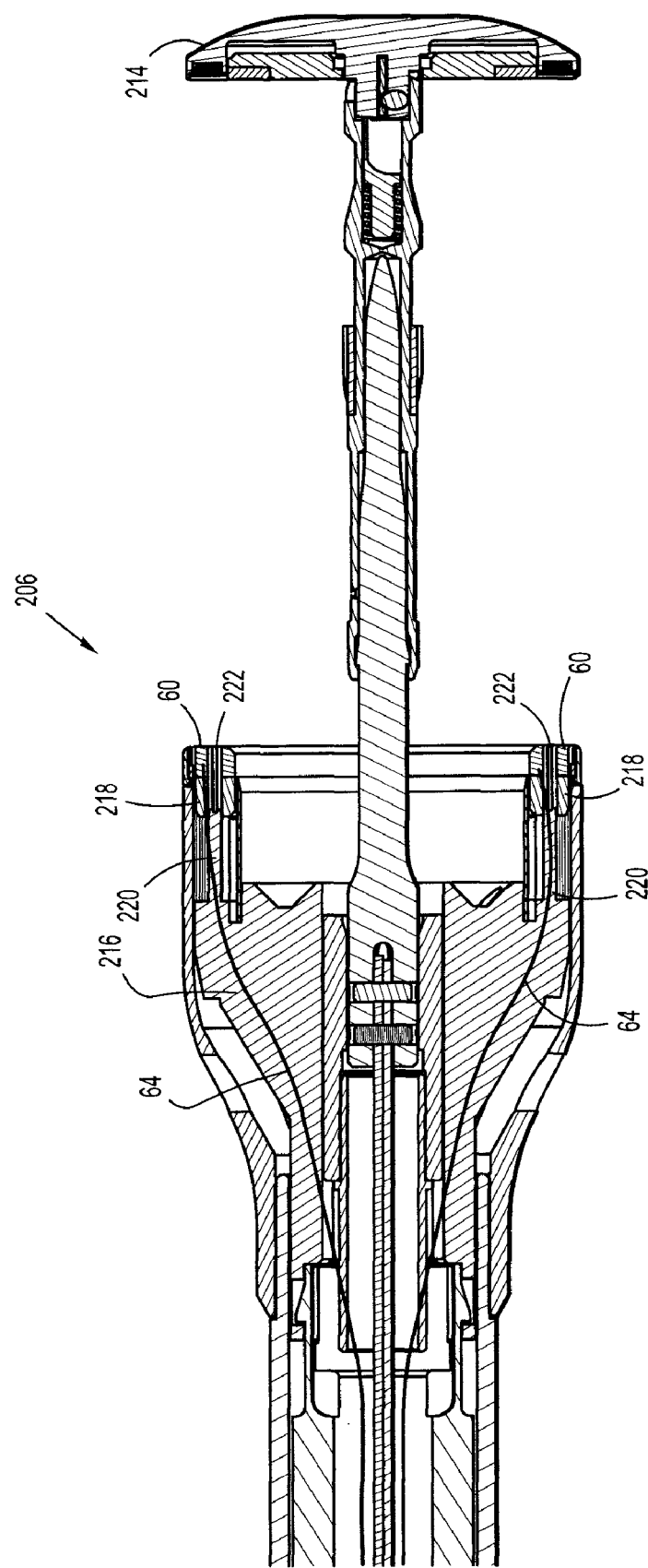
FIG. 13 is a side cross-sectional view of the distal portion of the surgical stapling instrument shown in FIG. 10 with transducers attached to the staple slots.

With reference to FIG. 13, another embodiment of tool assembly 206 includes transducers 60 positioned adjacent to a distal portion of retention slots 218. Wires 64 operatively couple transducers 60 to power source 12 (see FIG. 10). Transducers 60 effect vibrations on retention slots 218 and staples 222 when energized by power source 12. The vibrations of transducers 60 cause the vibration of staples 222 and reduce friction. Due to the decrease in friction, staples 222 requires less the force to penetrate tissue. The vibrations of staples 222 also impart a component of displacement in the direction of the tissue. This component of displacement significantly facilitates the penetration of tissue by staples 222.

Figure 14:
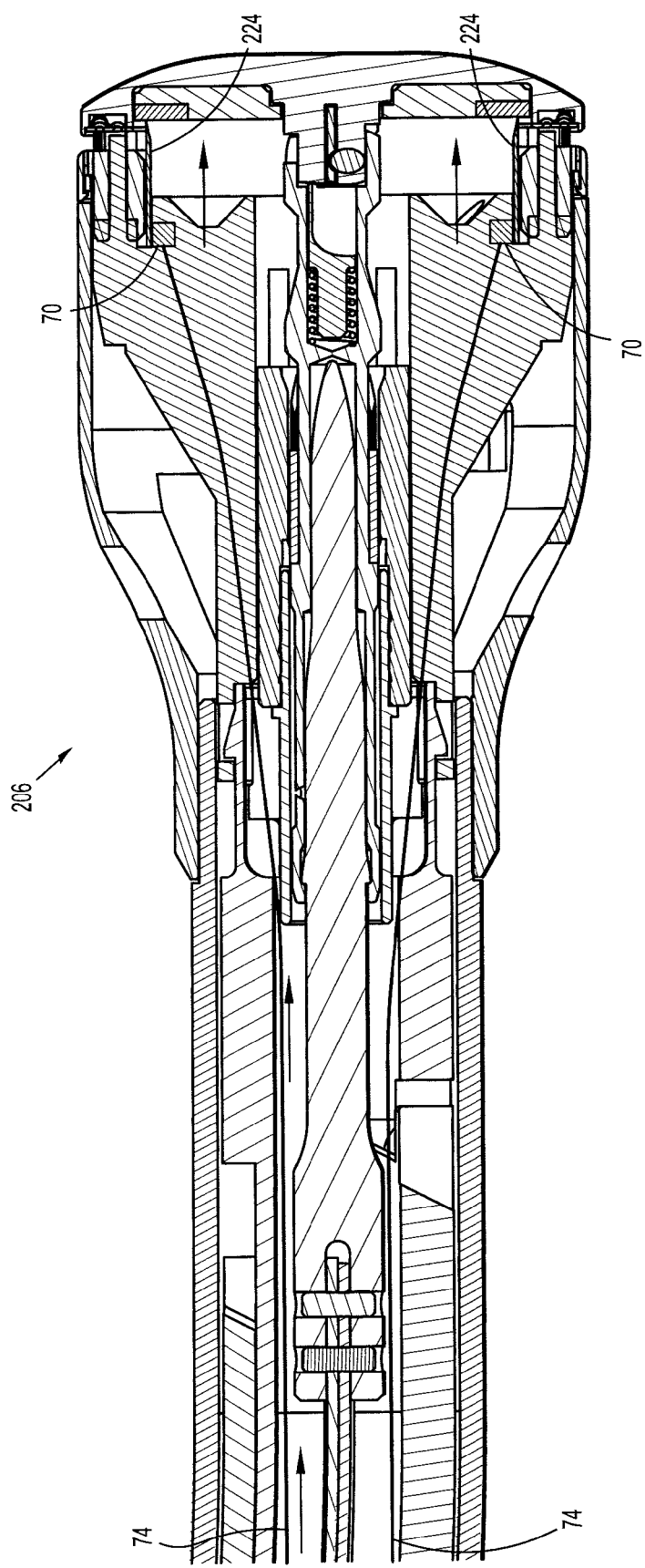
FIG. 14 is a side cross-sectional view of the distal portion of the surgical stapling instrument shown in FIG. 10 with transducers located adjacent to the knife.

With reference to FIG. 14, a further embodiment of tool assembly 206 includes a knife 224 operatively secured to staple pusher 216. Knife 224 is adapted to sever tissue when staple pusher 216 advances distally. Tool assembly 206 also has a plurality of transducers 70 positioned adjacent to knife 224. Wires 74 operatively connect transducers 70 to power source 12 (see FIG. 10). Transducer 70 is configured to convert the energy supplied by power source 12 into mechanical vibrations.

In use, the vibrations of the transducers 70 propagate through knife 224. The vibrations of knife 224 then decrease friction and, consequently, reduce the amount of force necessary to cut through tissue. The vibration of knife 224 also aids hemostasis and reduces bleeding.

Figure 15:
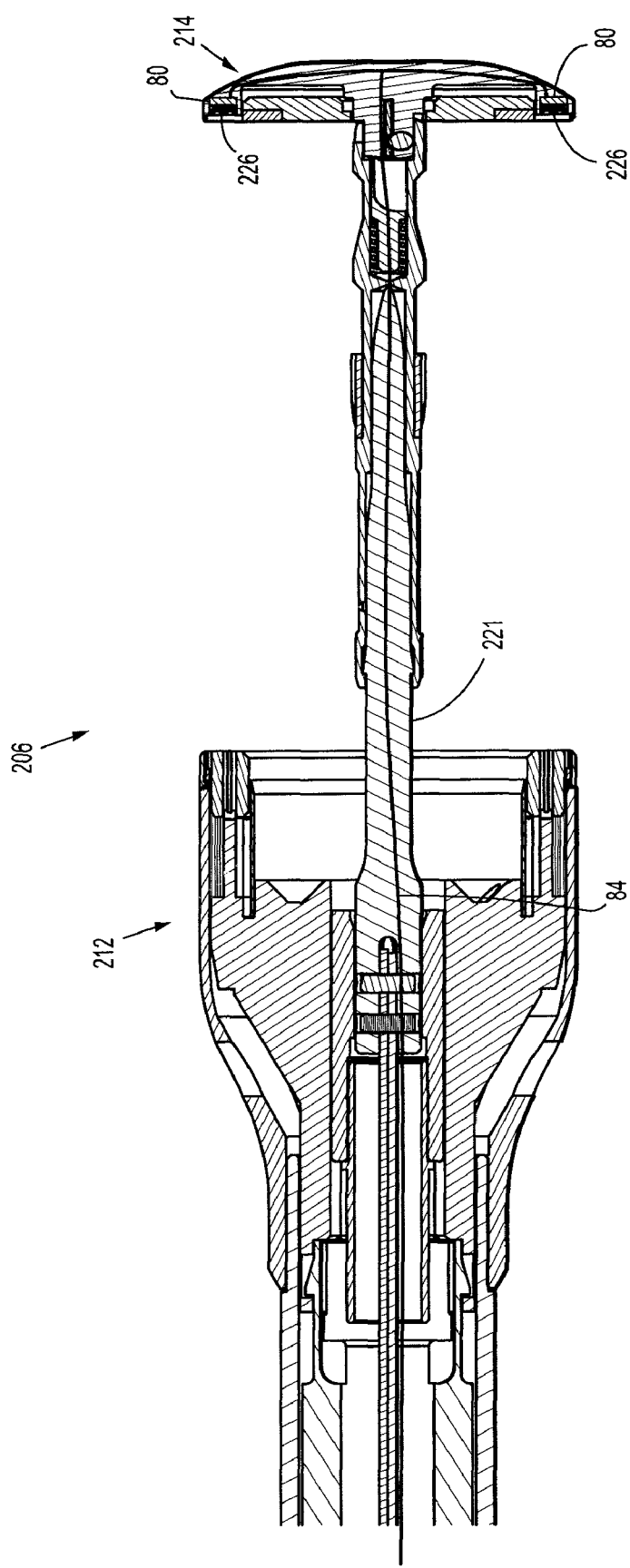
FIG. 15 is a side cross-sectional view of the distal portion of the surgical stapling instrument shown in FIG. 10 having transducers positioned on the anvil assembly and wires operatively connecting a power source to the transducers.

With reference to FIG. 15, still another embodiment of tool assembly 206 has transducers 80 located on the anvil assembly 214. Specifically, transducers 80 are positioned adjacent to staple deforming cavities 226 of anvil assembly 214. Wires 84 extend through cartridge assembly 212 to connect transducers 80 to power source 12 (see FIG. 10). Alternatively, power source 12 may be electrically coupled to transducers 80 through shaft 221 of cartridge assembly 212. Power source 12 supplies energy to transducers 80. Transducers 80 are configured to effect vibrations when energized by power source 12.

In operation, transducers 80 vibrate upon receiving electrical energy from power source 12. The vibrations of transducers 80 travel through anvil assembly 214 and facilitate the deformation of staples 222. Also, the vibrations aid the stapling process by reducing friction inside cartridge assembly 212 and anvil assembly 214. Consequently, the vibrations of transducers 80 decreases the amount of force required to penetrate tissue. Overall, the vibrations of transducer 80 and anvil assembly 214 significantly facilitate the penetration and formation of staples in tissue.

Figure 16:
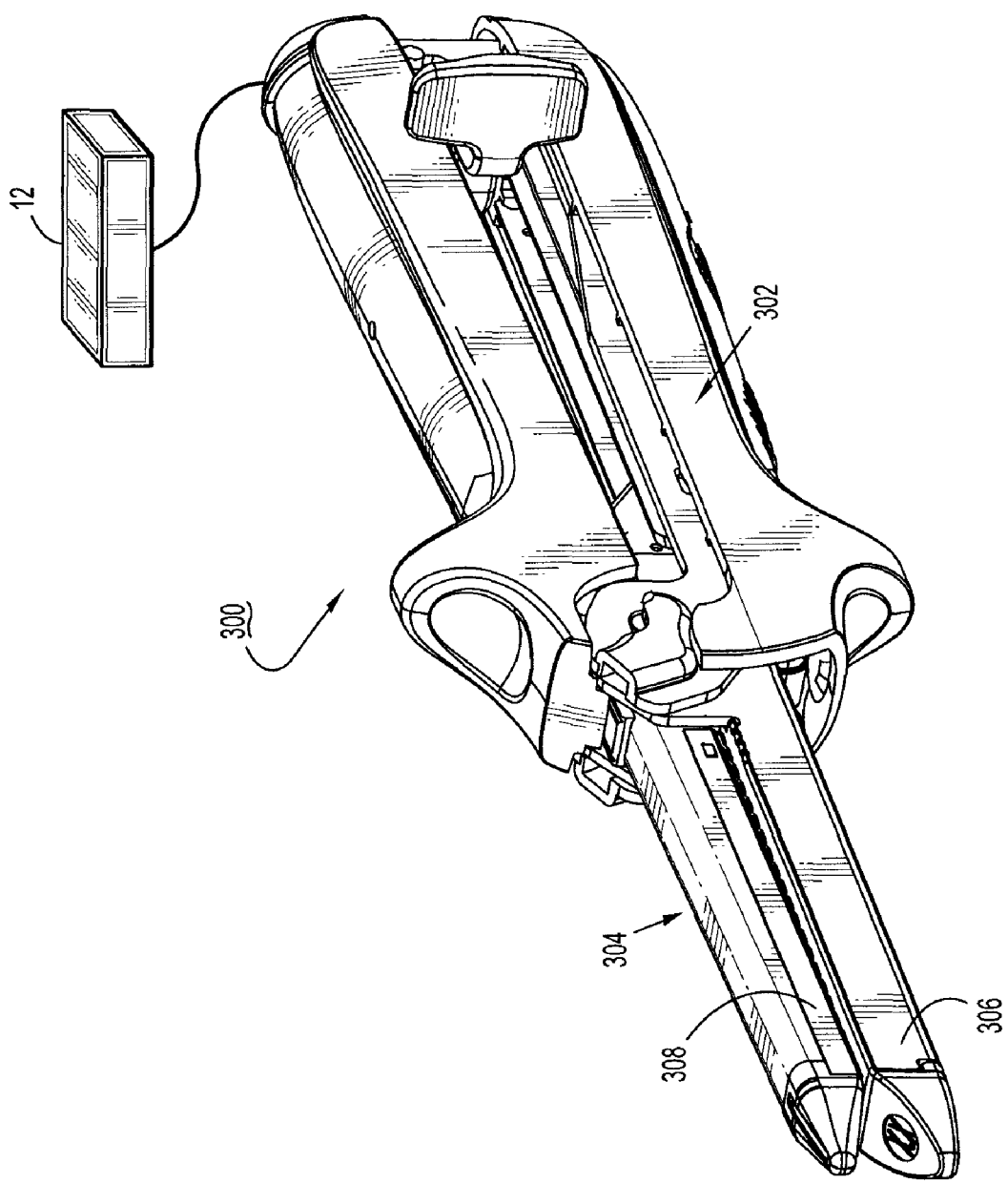
FIG. 16 is a perspective view of a surgical stapling instrument according to an embodiment of the present disclosure with a power source operatively coupled thereto.
Figure 17:
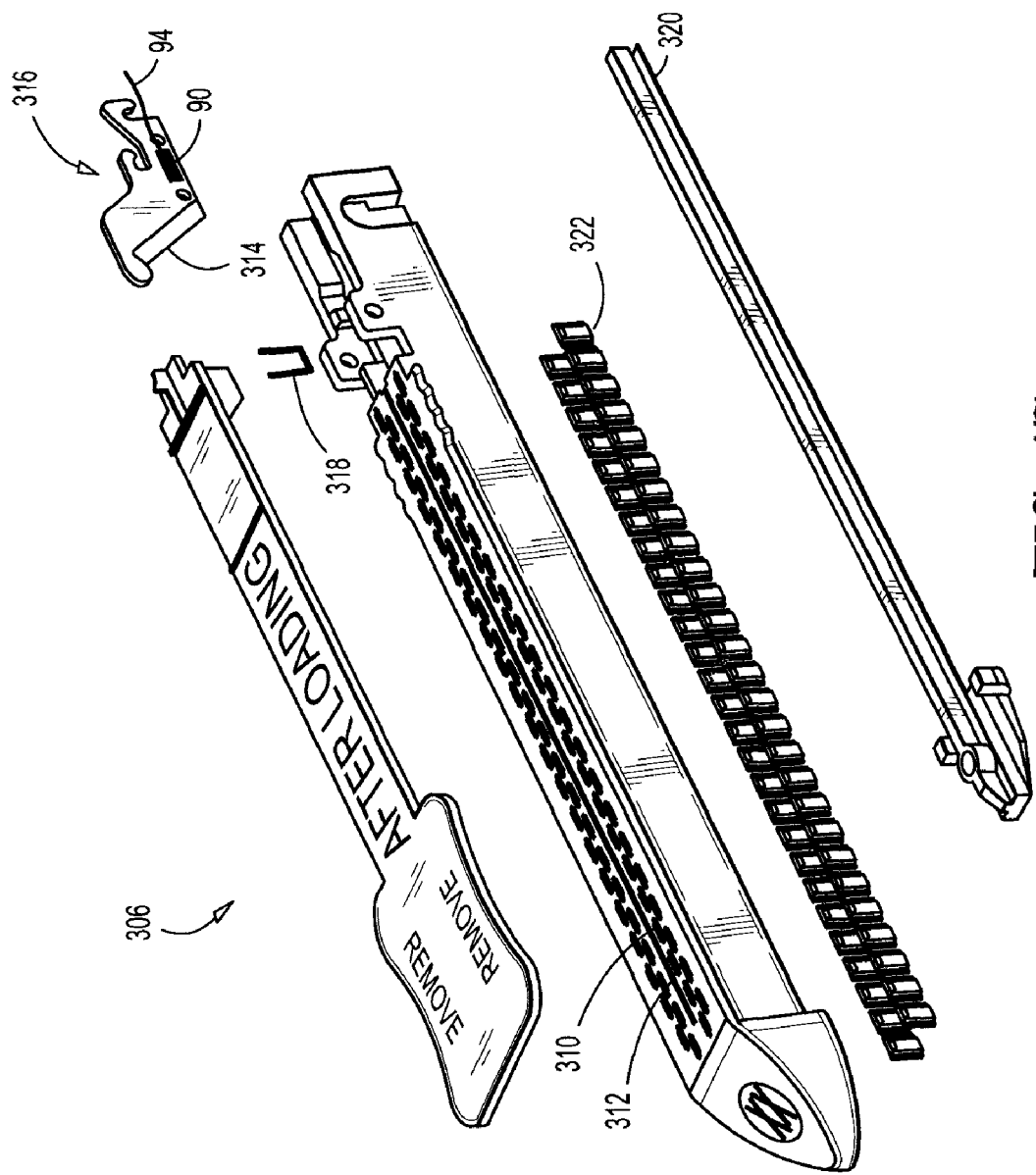
FIG. 17 is a perspective exploded view of the cartridge assembly of the surgical stapling instrument shown in FIG. 16 with a transducer located on the knife mount.

With reference to FIGS. 16 and 17, a surgical stapling instrument in accordance with an embodiment of the present disclosure is generally designated as 300. Surgical stapling instrument 300 has a handle assembly 302 operatively connected to a tool assembly 304. Tool assembly 304 includes a cartridge assembly 306 and anvil assembly 308. Cartridge assembly 306 and anvil assembly 308 are configured to move between an open position and a closed position in response to an actuation of handle assembly 302. U.S. Pat. No. 7,293,685, the entire contents of which is incorporated by reference herein, describes in detail the construction and operation of surgical stapling instrument 300. In particular, cartridge assembly 306 has a plurality of retention slots 310 arranged in rows, a knife channel 312 positioned between the rows of retention slots 310, a knife 314 supported by a knife mount 316, and an axial drive assembly 320. Each retention slot 310 is adapted to receive a staple 318 and a staple pusher 322. Knife channel 312 is adapted to slidably receive knife 314 and knife mount 316. In operation, the actuation of handle assembly 302 moves axial drive assembly 320 in a distal direction. The translation of the axial drive assembly 320 moves knife mount 316 along knife channel 312 and advances staple pushers 322 upwardly. As staple pushers 322 move upwardly, staples 318 eject from cartridge assembly 306. During the firing process, knife 316 cuts tissue and staples 318 fasten tissue.

In one embodiment, a transducer 90 is positioned on knife mount 316 for effecting vibrations on knife 314. A wire 94 operatively connects transducer 90 to a power source 12 (see FIG. 16). Power source 12 supplies energy to transducer 90. Transducer 90 is configured to vibrate when energized by power source 12. Consequently, transducer 90 effects vibrations on knife mount 316 and knife 314.

In operation, transducer 90 vibrates when it receive electrical energy from power source 12. Since the vibrations of transducer 90 travels through knife mount 316 and knife 314, knife 314 vibrates while transducer 90 vibrates. The vibrations of knife 314 reduce friction. As a result, the amount of force required to cut tissue decreases. In addition, the vibrations of knife 316 reduces bleeding while knife 314 cut through tissue.

Figure 18:
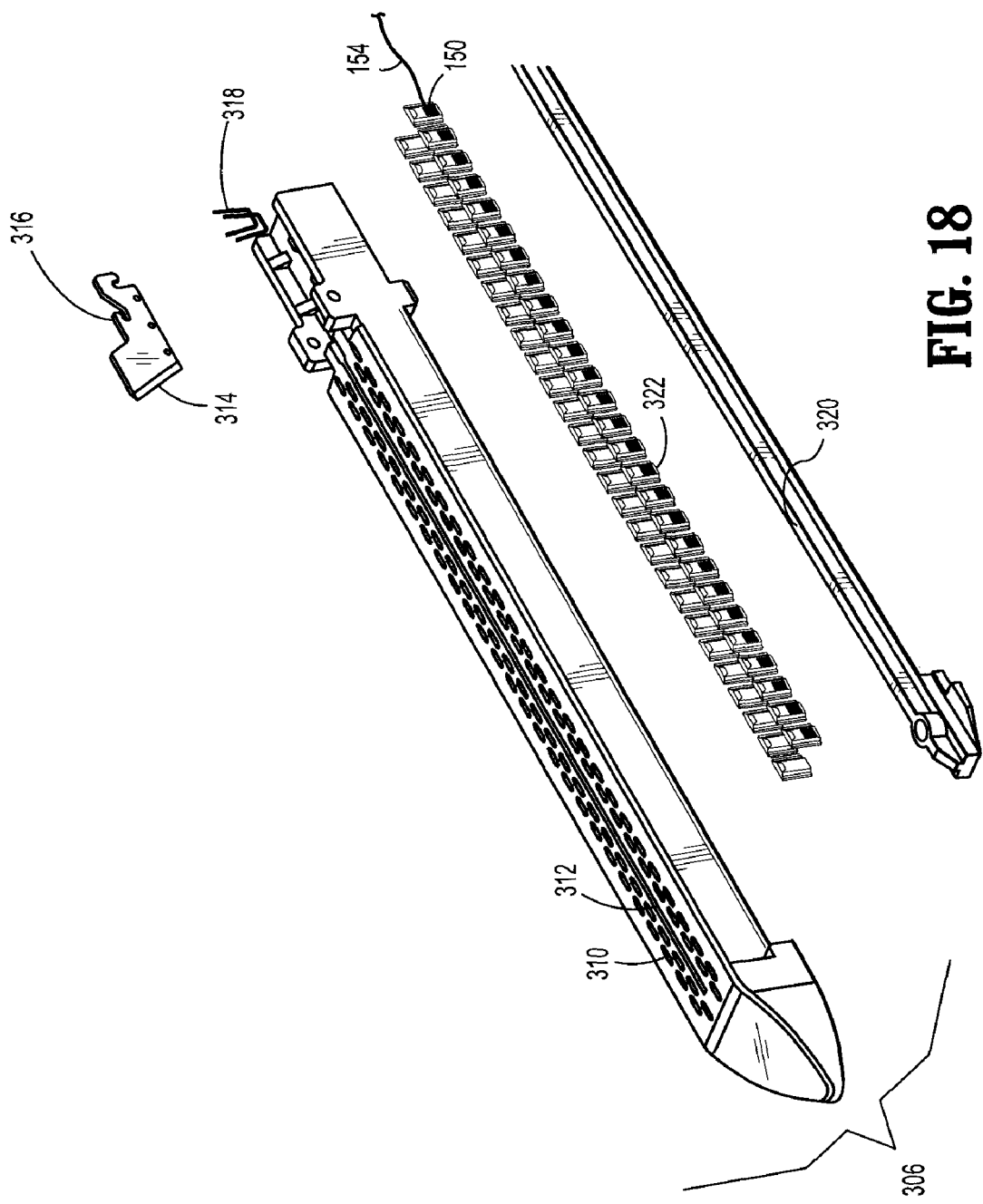
FIG. 18 is a perspective exploded view of the cartridge assembly of the surgical stapling instrument shown in FIG. 16 with transducers positioned on the staple pushers.

With reference to FIG. 18, another embodiment of cartridge assembly 306 is shown and includes a transducer 150 positioned on each staple pusher 322. Wire 154 operatively connects each transducer 150 to power source 12 (see FIG. 16). Power source 12 supplies energy to transducers 150.

In use, transducers 150 vibrate when energized by power source 12. Transducers 150 transmit its vibrations to staple pushers 322, thereby enhancing the stapling process. Particularly, the vibrations on staple pushers 322 decreases friction and therefore reduce the amount of force required to eject staples 318. Thus, staples are able to penetrate tissue using less force.

Figure 19:
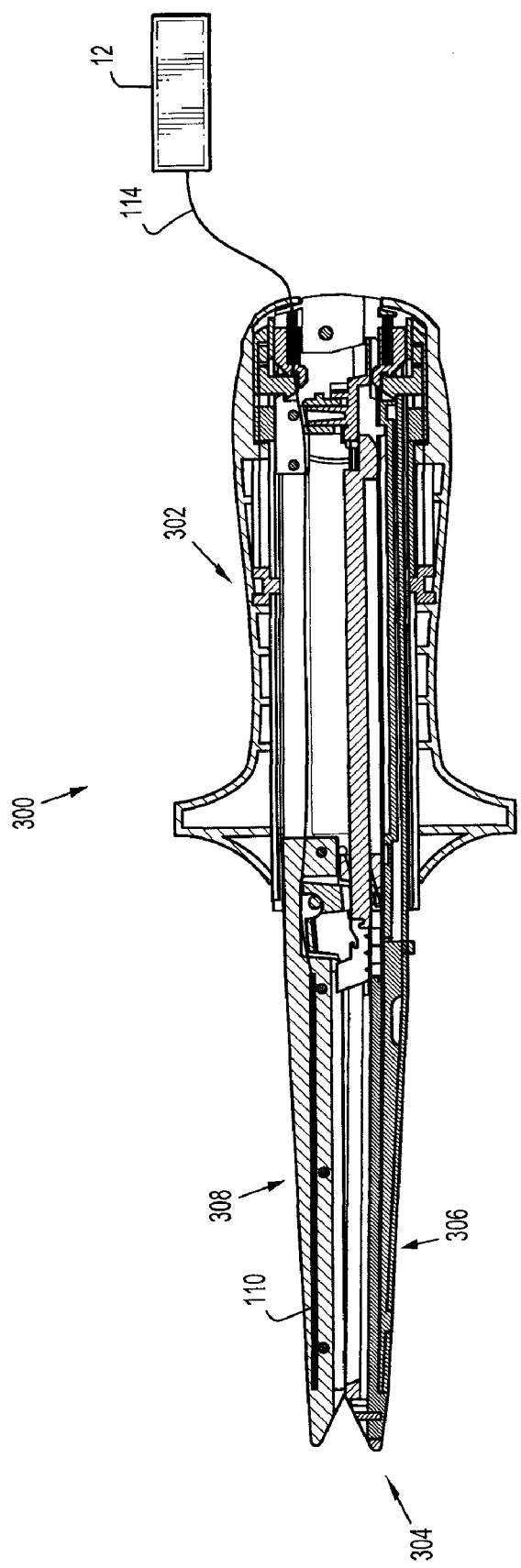
FIG. 19 is a side cross-sectional view of the surgical stapling instrument shown in FIG. 16 with a transducer located in the anvil assembly.

With reference to FIG. 19, another embodiment of surgical stapling instrument 300 includes a transducer 110 extending along at least a portion of the length of anvil assembly 308. Wires 114 operatively connect transducer 110 to power source 12. Power source 12 supplies energy to transducer 110. Transducer 110 is configured to vibrate and effect vibrations on anvil assembly 308 when it receives energy from power source 12. In an alternative embodiment, surgical stapling instrument 300 may include an array of transducers positioned along the length of anvil assembly 308. In this embodiment, the transducers are powered sequentially for producing a linear wave of vibrations.

During operation, transducer 110 vibrates and causes the vibration of anvil assembly 308. The vibrations of anvil assembly 308 decrease friction between anvil assembly 308 and cartridge assembly 306 and effectively reduce the amount of force required to clamp tissue and fire the staples. The vibrations of transducer 110 also intermittently displace anvil assembly 308 in the direction of the clamped tissue, thereby decreasing the amount of force necessary to penetrate tissue with the staples.

Figure 20:
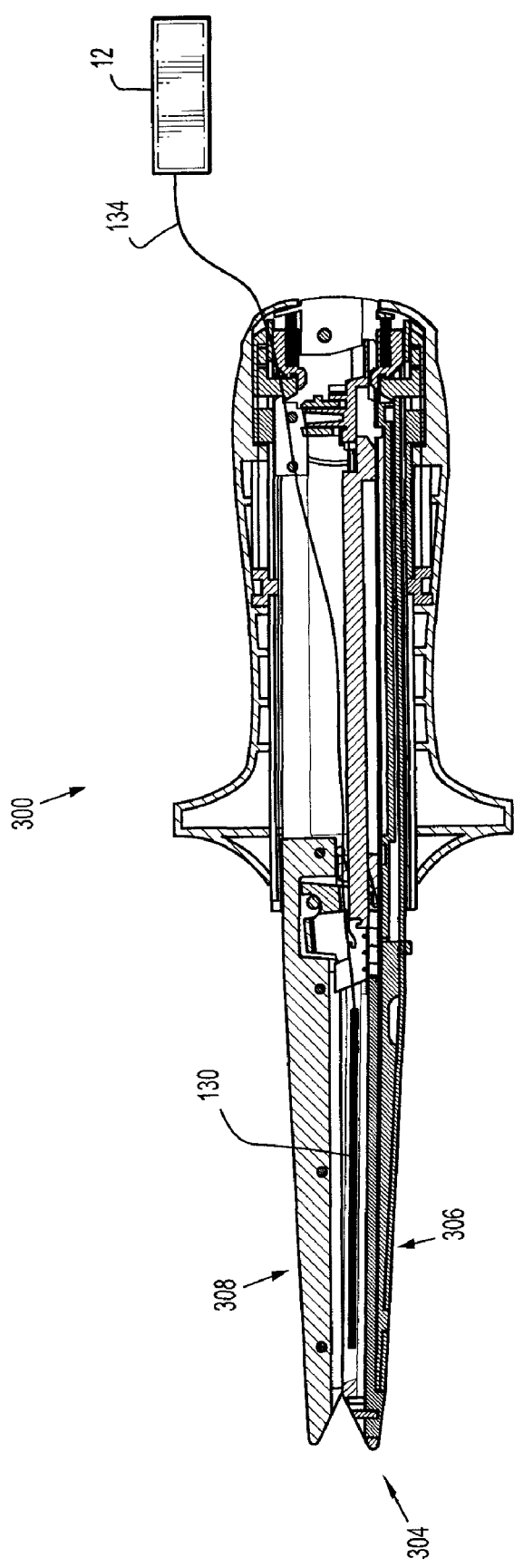
FIG. 20 is a side cross-sectional view of the surgical stapling instrument shown in FIG. 16 with a transducer located in the cartridge assembly.

With reference to FIG. 20, a further embodiment of surgical stapling instrument 300 incorporates a transducer 130 positioned along at least a portion of the length of cartridge assembly 306. Transducer 130 is operatively coupled to power source 12 through a wire 134. Power source 12 supplies energy to transducer 130. Alternatively, surgical stapling instrument 300 includes an array of transducers disposed along the length of cartridge assembly 306. These transducers may be sequentially activated to produce a linear wave of vibrations.

When energy is supplied to transducer 130, transducer 130 vibrates and effects vibrations on cartridge assembly 306. The vibrations of cartridge assembly 306 decreases friction between anvil assembly 308 and cartridge assembly 306 and effectively reduce the amount of force required to clamp tissue and fire the staples. The vibrations of transducer 130 also impart a displacement component in the direction of the clamped tissue, thereby decreasing the amount of force necessary to penetrate tissue with the staples.

Figure 21:
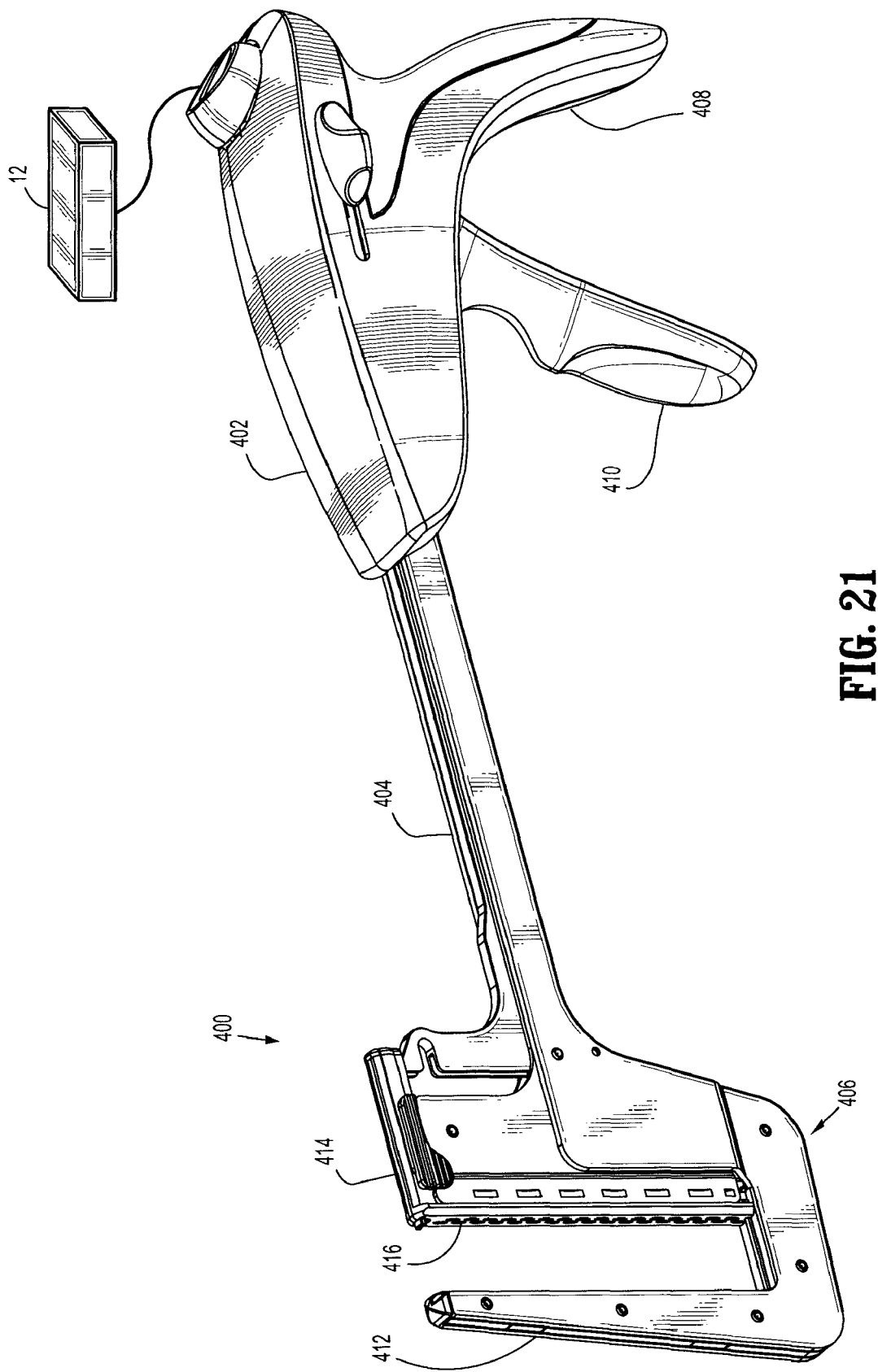
FIG. 21 is a perspective view of a surgical stapling instrument constructed in accordance with an embodiment of the present disclosure with a power source operatively connected thereto.
Figure 24:
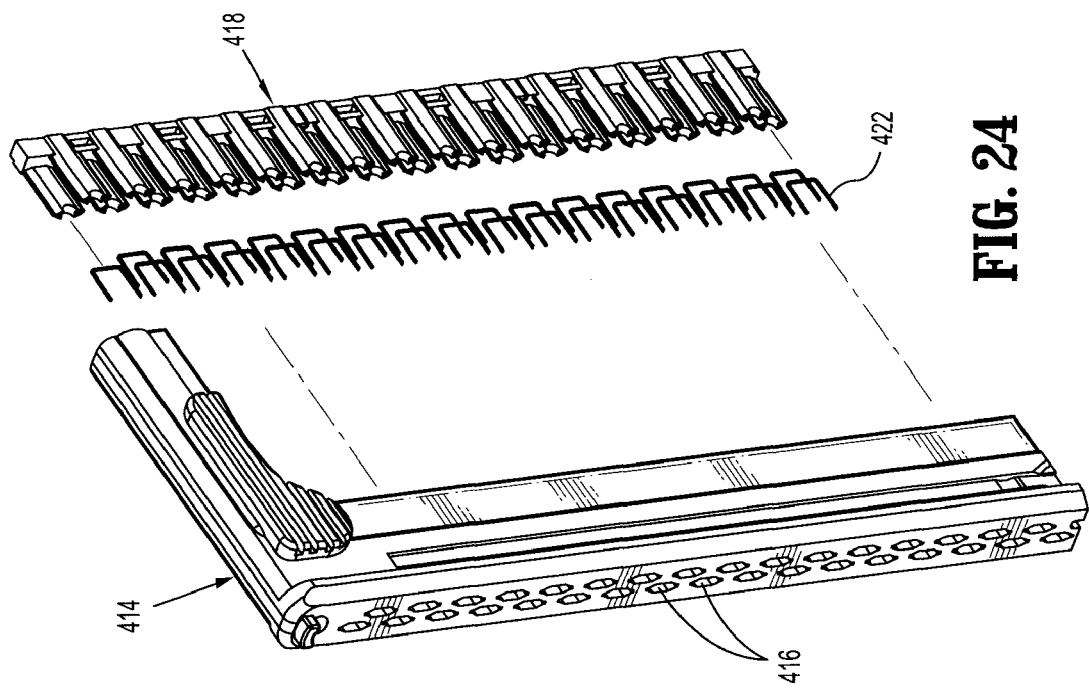
FIG. 24 is a perspective exploded view of a portion of the cartridge assembly of the surgical stapling instrument illustrated in FIG. 21.

With reference to FIG. 21, a surgical stapling instrument according to another embodiment of the present disclosure is generally designated as 400. U.S. Pat. No. 7,275,674, the contents of which are incorporated by reference in their entirety, describes in detail the construction and operation of the surgical stapling instrument 400. Briefly, surgical stapling instrument 400 includes a handle assembly 402, a central body portion 404, a tool assembly 406, and a power source 12. Handle assembly 402 has a stationary handle member 408 and a movable handle member 410. In use, movable handle member 410 pivots relative to stationary handle member 408 to actuate tool assembly 406. Central body portion 404 interconnects tool assembly 406 and handle assembly 402. Tool assembly 406 includes an anvil assembly 412 and a cartridge assembly 414. Cartridge assembly 414 moves in relation to anvil assembly 412 upon actuation of handle assembly 402. During operation, cartridge assembly 414 specifically moves between an open position and a closed position to clamp tissue toward anvil assembly 412. In addition, cartridge assembly 414 ejects staples in response to an actuation of handle assembly 402. Cartridge assembly 414 includes retention slots 416 adapted to receive staples and staple pushers 418 (FIG. 22) configured to eject staples, as seen in FIG. 24.

Figure 22:
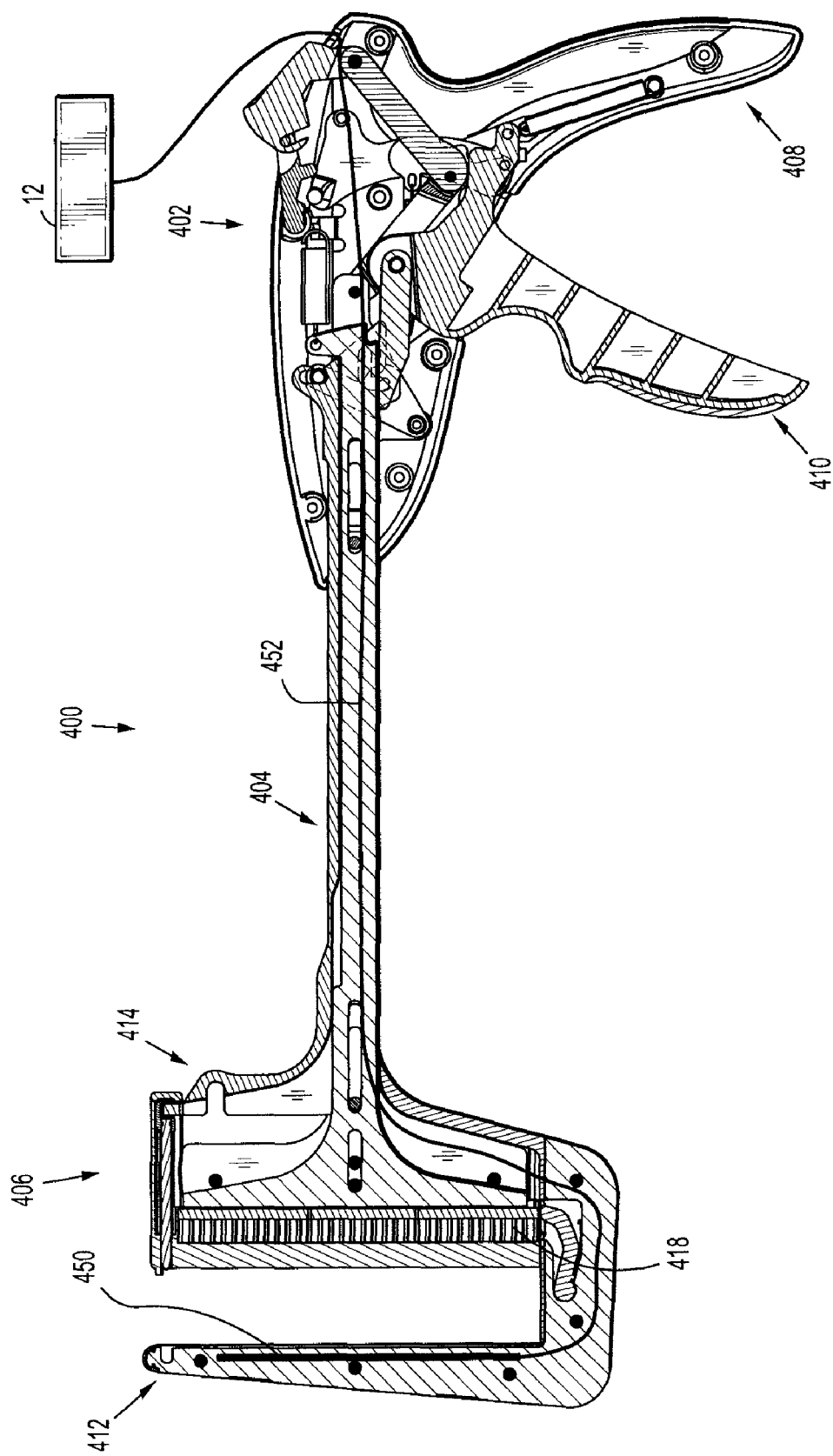
FIG. 22 is side cross-sectional view of the surgical stapling instrument shown in FIG. 21 including a transducer positioned within the anvil assembly.

Referring to FIG. 22, anvil assembly 412 includes at least one transducer 450 operatively connected to power source 12. A wire 452 connects power source 12 to transducer 450. Power source 12 supplies energy to transducer 450. Transducer 450 is configured to vibrate and effect vibrations on anvil assembly 412 when it receives energy from power source 12.

In operation, transducers 450 effects vibrations on tool assembly 406. The vibrations of tool assembly 406 reduce friction therein and decrease the amount of force necessary to actuate tool assembly 406 and fasten tissue. Also, the vibrations of tool assembly 406 produce a displacement component in the direction of the clamped tissue, thereby improving staple tissue penetration.

Figure 23:
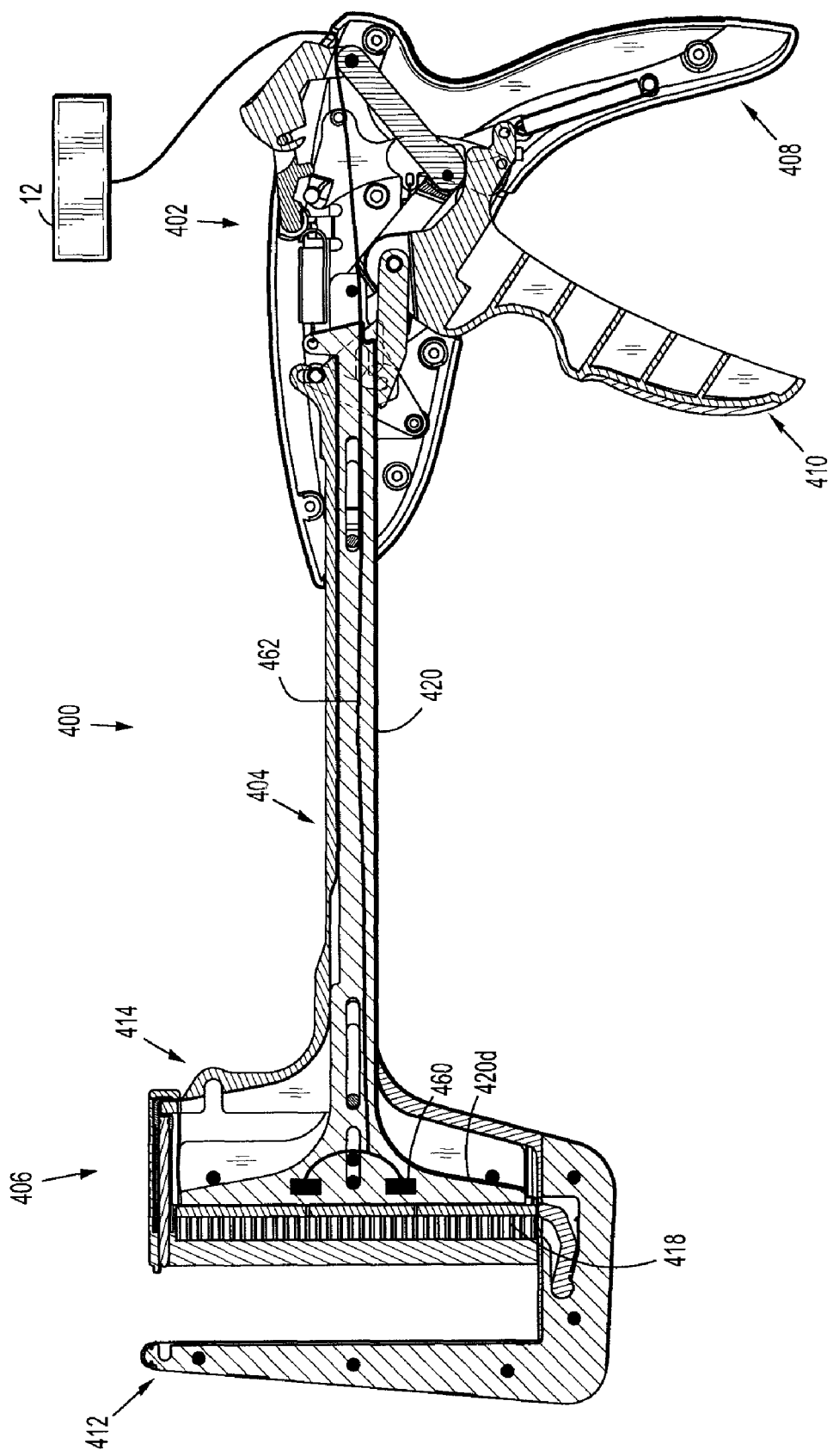
FIG. 23 is a side cross-sectional view of the surgical stapling instrument shown in FIG. 21 having a plurality of transducers located in the cartridge assembly.

With reference to FIG. 23, another embodiment of surgical stapling instrument 400 includes at least one transducer disposed on a distal portion 420d of an axial drive assembly 420. A wire 462, or any other suitable electrical coupler, operatively connects transducers 460 to power source 12. Power source 12 supplies energy to transducers 460.

When power source 12 supplies energy to transducers 460, transducers 460 vibrates and effect vibrations on cartridge assembly 414. The vibrations of transducers 460 travel throughout cartridge assembly 414 and reduce friction. Therefore, the reduced friction decreases the amount of force required to staple tissue. In addition, the vibrations of transducers 460 impart a displacement component in the direction of the tissue and thus facilitate the penetration of tissue by the staples.

Figure 25:
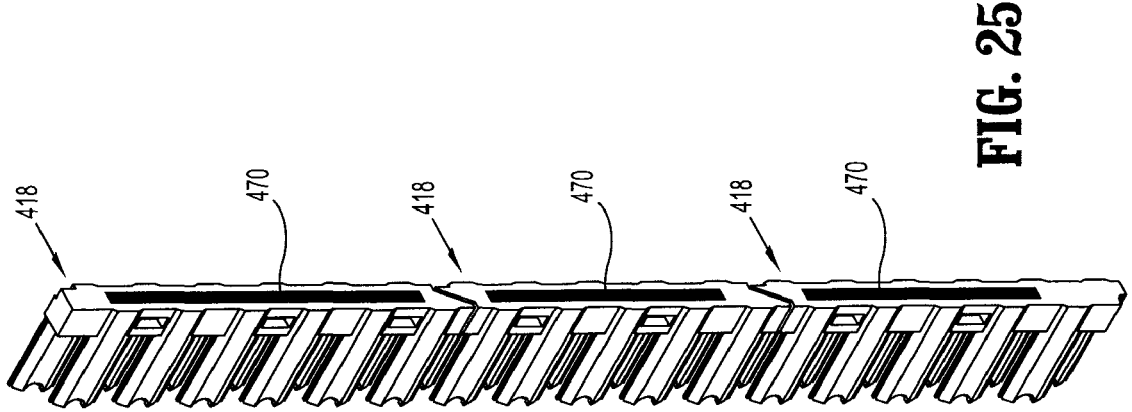
FIG. 25 is a perspective view of the staple pushers of the cartridge assembly of the surgical stapling instrument shown in FIG. 21 with transducers attached thereto.

With reference to FIGS. 24 and 25, another embodiment of tool assembly 406 includes transducers 470 operatively attached to staple pushers 418. As discussed above, staple pushers 418, which are located within cartridge assembly 414, are adapted to eject staples 422 from tool assembly 406. Transducers 470 are operatively coupled to power source 12 and are configured to vibrate when energized by power source 12.

During operation, transducers 470 vibrate when they receive electrical energy from power source 12. The vibrations of transducers 470 propagate through staple pushers 418. In turn, the vibrations of staple pushers 418 effectively reduce the amount of force required to penetrate staples through tissue. Additionally, the vibrations of staple pushers 418 also impart a displacement component in the direction of the tissue. This displacement component also facilitates the penetration of staples through tissue.

All the transducers disclosed herein may be made by piezoelectric ceramic elements, electric motors, solenoids, springs, any combination thereof, or any other device capable of producing vibrations. During operation of any of the disclosed surgical stapling instruments, a user activates the transducers before or while firing the surgical stapling instrument. At this point, the transducers vibrate a component of the surgical stapling instrument. This vibration reduces the frictional forces experienced by the surgical stapling instrument and, consequently, decreases the amount of force necessary to cut or staple tissue.

It will be understood that various modifications may be made to the embodiments disclosed herein. For example, although the transducer assemblies disclosed herein are operatively associated with a particular surgical stapling instrument, these transducer assemblies may be incorporated into any suitable medical stapler including those instruments disclosed in the following U.S. patents: U.S. Pat. Nos. 7,303,107, 7,296,724, 7,293,685, 7,278,562, 7,275,674, 7,237,708, and 7,234,624, all of which are hereby incorporated by reference in their entirety. Further, transducers may be formed by electric motors, solenoids, springs, or any other suitable device capable of producing mechanical vibrations. In addition, the embodiments described herein may be combined to form a surgical stapling instrument with more than one vibrating component. For instance, transducers may be located in the anvil assembly and the knife. Alternatively, a surgical stapling instrument may contain transducers in the cartridge assembly, the knife edge of the axial drive assembly, and the cartridge assembly. Therefore, the above description should not be construed as limiting, but merely as exemplifications of embodiments. Those skilled in the art will envision other modifications within the scope and spirit of the claims appended hereto.

What is claimed is:

1. An end effector for use with a surgical stapling instrument, the end effector comprising:
a cartridge assembly housing a plurality of fasteners;
an anvil assembly operatively connected to the cartridge assembly, the anvil assembly and the cartridge assembly being movable between open and closed positions; and
a plurality of transducers located in the end effector, the plurality of transducers operably connected to at least one of the cartridge assembly and the anvil assembly and being adapted to sequentially effect vibrations along at least one of the anvil assembly and the cartridge assembly.

2. The end effector according to claim 1, wherein the plurality of transducers effect vibrations to reduce the resistance of the tissue to the fasteners as the fasteners penetrate the tissue.

3. The end effector according to claim 1, further comprising a power source disposed in electro-mechanical cooperation with the plurality of transducers.

4. The end effector according to claim 1, wherein the cartridge assembly includes a plurality of retentions slots each adapted to hold at least one fastener of the plurality of fasteners and at least one in the plurality of transducers is operatively associated with at least one of the retention slots.

5. The end effector according to claim 2, wherein the cartridge assembly includes a plurality of pushers adapted to drive the fasteners toward the anvil assembly upon actuation of a driving member, each of the plurality of transducers being disposed on and operatively associated with at least one in the plurality of pushers and adapted to sequentially effect vibrations on the plurality of pushers and the corresponding fasteners upon actuation of the driving member to reduce the frictional forces between the fasteners and tissue.

6. The end effector according to claim 1, wherein the anvil assembly includes fastener deforming pockets and each of the plurality of transducers is located adjacent to and operatively associated with at least one of the fastener deforming pockets.

7. The end effector according to claim 2, wherein the plurality of transducers is disposed inside the anvil assembly and adapted to sequentially effect vibrations to tissue clamped between the anvil assembly and the cartridge assembly upon actuation of an axial drive assembly through the end effector to reduce the frictional forces therebetween.

8. The end effector according to claim 2, further comprising an actuation sled adapted to move longitudinally through the cartridge assembly upon actuation of an actuating member of the surgical stapling instrument to actuate a plurality of pushers to urge the fasteners toward the anvil assembly, wherein at least one in the plurality of transducers is located on the actuation sled and adapted to sequentially effect vibrations on the plurality of pushers and the corresponding fasteners as the actuation sled moves longitudinally through the cartridge assembly to reduce the frictional forces between the tissue and the fasteners.

9. The end effector according to claim 2, wherein the plurality of transducers is disposed along at least a portion of a length of the cartridge assembly and is adapted to sequentially effect vibrations on the cartridge assembly and the fasteners to reduce the frictional forces of tissue in contact with the cartridge assembly.

10. The end effector according to claim 2, further comprising a knife disposed in the cartridge assembly and configured to move longitudinally through the cartridge assembly, wherein at least one in the plurality of transducers is located on the knife to effect vibrations on the knife to reduce the frictional forces as the knife translates through tissue.

11. A surgical instrument, comprising:
a handle assembly;
an axial drive assembly operably coupled to the handle assembly, wherein the axial drive assembly is configured to move longitudinal upon actuation of the handle assembly;
an end effector operatively connected to the axial drive assembly, the end effector having an anvil assembly and a cartridge assembly, the cartridge assembly being configured to house a plurality of fasteners, wherein the anvil assembly and the cartridge assembly are adapted to move relative to each other between an open position and a closed position; and
a plurality of transducers located in the end effector, the plurality of transducers being configured to sequentially effect vibrations along at least a portion of the end effector.

12. The surgical instrument according to claim 11, further comprising a power source disposed in electro-mechanical cooperation with plurality of transducers.

13. The surgical instrument according to claim 11, wherein at least one in the plurality of transducers is positioned on the axial drive assembly.

14. The surgical instrument according to claim 11, wherein the cartridge assembly includes a plurality of retentions slots each adapted to hold at least one fastener of the plurality of fasteners and at least one in the plurality of transducers is operatively associated with at least one of the retention slots.

15. The surgical instrument according to claim 11, wherein the cartridge assembly includes a plurality of pushers adapted to drive the fasteners toward the anvil assembly upon longitudinal movement of an actuation sled operably coupled to the axial drive assembly, the plurality of transducers being disposed on and operatively associated with the plurality of pushers and adapted to sequentially effect vibrations on the plurality of pushers upon longitudinal movement of the actuation sled.

16. The surgical instrument according to claim 15, further comprising a power source disposed in electro-mechanical cooperation with the actuation sled, the actuation sled including electrical contacts adapted to establish an electrical connection between the actuation sled and the plurality of transducers disposed on the plurality of pushers as the actuation sled moves longitudinally through the cartridge assembly to engage the plurality of pushers.

17. The surgical instrument according to claim 11, wherein the anvil assembly includes fastener deforming pockets and at least one in the plurality of transducers is operatively associated with at least one of the fastener deforming pockets.

18. The surgical instrument according to claim 11, wherein the plurality of transducers is disposed inside the anvil assembly and is adapted to sequentially effect vibrations to tissue clamped between the anvil assembly and the cartridge assembly upon longitudinal movement of the axial drive assembly to reduce frictional forces therebetween.

19. The surgical instrument according to claim 11, further comprising an actuation sled operably coupled to the axial drive assembly and adapted to move longitudinally through the cartridge assembly to urge the fasteners toward the anvil assembly, wherein at least one in the plurality of transducers is located on the actuation sled and adapted to sequentially effect vibrations to the fasteners upon longitudinal movement of the axial drive assembly to reduce the frictional forces between the fasteners and tissue.

20. The surgical instrument according to claim 11, further comprising a knife disposed in the cartridge assembly and configured to move longitudinally, wherein at least one in the plurality of transducers is located on the knife and is adapted to effect vibrations on the knife to reduce the frictional forces as the knife translates through tissue.

* * * * *